US012178940B2

(12) United States Patent
Gurtner et al.

(10) Patent No.: US 12,178,940 B2
(45) Date of Patent: *Dec. 31, 2024

(54) CONTROLLED HYDROGEL DELIVERY OF FOCAL ADHESION KINASE INHIBITOR FOR DECREASED SCAR FORMATION

(71) Applicant: THE BOARD OF TRUSTEES OF THE LELAND STANFORD JUNIOR UNIVERSITY, Stanford, CA (US)

(72) Inventors: Geoffrey C. Gurtner, Portola Valley, CA (US); Sun Hyung Kwon, Stanford, CA (US); Mohammed Inayathullah Nazir Ahmed, Santa Clara, CA (US); Jayakumar Rajadas, Cupertino, CA (US)

(73) Assignee: THE BOARD OF TRUSTEES OF THE LELAND STANFORD JUNIOR UNIVERSITY

(*) Notice: Subject to any disclaimer, the term of this patent is extended or adjusted under 35 U.S.C. 154(b) by 1043 days.

This patent is subject to a terminal disclaimer.

(21) Appl. No.: 17/049,359

(22) PCT Filed: May 16, 2019

(86) PCT No.: PCT/US2019/032697
§ 371 (c)(1),
(2) Date: Oct. 21, 2020

(87) PCT Pub. No.: WO2019/222520
PCT Pub. Date: Nov. 21, 2019

(65) Prior Publication Data
US 2021/0361833 A1   Nov. 25, 2021

Related U.S. Application Data

(60) Provisional application No. 62/848,515, filed on May 15, 2019, provisional application No. 62/672,513, filed on May 16, 2018.

(51) Int. Cl.
*A61L 27/56* (2006.01)
*A61L 27/24* (2006.01)
*A61L 27/52* (2006.01)
*A61L 27/54* (2006.01)

(52) U.S. Cl.
CPC ............ *A61L 27/56* (2013.01); *A61L 27/24* (2013.01); *A61L 27/52* (2013.01); *A61L 27/54* (2013.01); *A61L 2300/204* (2013.01); *A61L 2430/18* (2013.01); *A61L 2430/34* (2013.01)

(58) Field of Classification Search
CPC .......... A61L 27/56; A61L 27/24; A61L 27/52; A61L 27/54; A61L 2300/204; A61L 2430/18; A61L 2430/34
See application file for complete search history.

(56) References Cited

U.S. PATENT DOCUMENTS

| 9,636,362 B2 | 5/2017 | Gurtner et al. |
| 9,655,967 B2 | 5/2017 | Gurtner et al. |
| 2008/0033334 A1 | 2/2008 | Gurtner et al. |
| 2011/0305745 A1* | 12/2011 | Gurtner ............... A61L 27/48 424/443 |
| 2013/0165463 A1* | 6/2013 | Gurtner ............... A61K 45/06 514/275 |
| 2014/0072613 A1 | 3/2014 | Lander et al. |

FOREIGN PATENT DOCUMENTS

| JP | 2003190206 | 7/2003 |
| JP | 2007513693 | 5/2007 |
| WO | 2012063947 | 5/2012 |

OTHER PUBLICATIONS

Baumann M. et al. "Quantatative Analysis of Burn Scars: Selecting Noninvasive Instruments for Clinical Evaluation" Wound Repair Regen. (2017) 25:4 A7.
Kwon, Sun Hyung et al. "Topical Delivery of a Focal Adhesion Kinase Inhibitor Results in Accelerated Wound Healing with Reduced Scarring in a Porcine Wound Model" Wound Repair Regen. (2018) 26:1 A33.
Wong, Victor et al. "Engineered Pullalan-Collagen Composite Dermal Hydrogels Improve Early Cutaneous Wound Healing" Tissue Eng. (2011) 17:5,6 631-644.
Aarabi et al.; Mechanical load initiates hypertrophic scar formation through decreased cellular apoptosis; The FASEB Journal; 21(12); pp. 3250-3261; Oct. 2007.
Andre et al.; Expression of an N-terminally truncated form of human focal adhesion kinase in brain; Biochemical and Biophysical Research Communications; 1901(1); pp. 140-147; Jan. 1993.
Bredfeldt et al.; Automated quantification of aligned collagen for human carcinoma prognosis; Journal of Pathology Informatics; 13 pages; retrieved from the internet (https://www.jpathinformatics.org/temp/JPatholInform5128-7254766_200907.pdf): Aug. 2014.
Bredfeldt et al.; Computational segmentation of collagen fibers from second-harmonic generation images of breast cancer; Journal of Biomedical Optics; 19(1); 016007-1-1016007-10; Jan. 2014.
Candes et al.; Fast discete curvelet transforms; Multiscale Modeling and Stimulation; 5(3); pp. 861-899; 44 pages; (Author Manuscript); Mar. 2006.
Gurtner et al.; Improving cutaneous scar formation by controlling the medanical environment: large animal and pahse I studies; Annals of Surgery; 254(2); pp. 217-225; Aug. 2011.
Gurtner et al.; Wound repair and regeneration; Nature; 453(7193); pp. 314-321; May 2008.

(Continued)

*Primary Examiner* — Snigdha Maewall
(74) *Attorney, Agent, or Firm* — Rimon PC

(57) ABSTRACT

The formation of scars at a wound site is reduced by contacting the wound site with an effective dose of an inhibitor of focal adhesion kinase (FAK) formulated in a pullulan hydrogel The release profile of the FAK inhibitor can be adjusted according to the nature of the wound, e.g., excisional wounds, burn wounds, etc.

14 Claims, 15 Drawing Sheets

(56) References Cited

OTHER PUBLICATIONS

Infante et al.; Safety, Pharmacokinetic, and pharmacodynamic phase 1 dose-escalation trial of PF-00562271, an inhibitor of focal adhesion kinase, in advanced solid tumors; Journal of Clinical Oncology; 30(13); pp. 1527-1533; May 2012.

Lim et al.; The embrace device significantly decreases scarring following scar revision surgery in a randomized controlled trial; Plaastic and Reconstructive Surgery; 133(2); pp. 398-405; 16 pages; (Author Manuscript); Feb. 2014.

Longaker et al.; A randomized controlled trial of the embrace advanced scar therapy device to reduce incisional scar formation; Plastic and Reconstructive Surgery; 134(3); pp. 536-546; 19 pages; (Author Manuscript); Sep. 2014.

Ma et al.; Controlled delivery of a focal adhesion kinase inhibitor results in accelerated wound closure with decreased scar formation; journal of Investigative Dermatology; 138(11); pp. 2452-2460; Nov. 2018.

Sultan et al.; Fat grafting accelerates revascularisation and decreases fibrosis following thermal injury; Journal of Plastic, Reconstructive and Aesthetic Surgery; 65(2); pp. 219-227; Feb. 2012.

Wang et al.; The mouse excisional wound splinting model including applications for stem cell transplantation; Nature Protocols; 8(2); pp. 302-309; Feb. 2013.

Wong et al.; Pullulan hydrogels improve mesenchymal stem cell delivery into high-oxidative-stress wounds; Macromolecular Bioscience; 11(11); pp. 1458-1466; 15 pages; (Author Manuscript); Nov. 2011.

Wong et al.; Engineered pullulan collagen composite dermal hydrogels improve early cutaneous wound healing; Yissue Engineering Part A; 17(5-6); pp. 631-644; Mar. 2011.

Wong et al.; Focal adhesion kinase links mechanical force to skin fibrosis via inflammatory signaling; Nature Medicine; 18(1); pp. 148-152; 13 pages; (Author Manuscript); Jan. 2012.

Wong et al.; Loss of keratinocyte focal adhesion kinase stimulates derman proteolysis through upregulation of MMP9 in wound healing; Annals of Surgery; 260(6); pp. 1138-1146; Dec. 2014.

Wong et al.; Mechanical force prolongs acute inflammation via t-cell-dependent pathways during scar formation; The FASEB Journal; 25(12); pp. 4498-4510; Dec. 2011.

Wong et al.; Pushing back: wound mechanotransduction in repair and regeneration; journal of Investigative Dermatology; 131(11); pp. 2186-2196; Nov. 2011.

Wong et al.; Surgical approaches to create murine models of human wound healing; Journal of Biomedicine and Biotechnology; vol. 2011; Article 969618; doi:10.1155/2011/969618; 8 pages; (year of pub. sufficiently earlier than effective US filing date and any foreign priority date) 2011.

Zhu et al.; Review of the female duroc/yorkshire pig model of human fibroproliferative scarring; Wound Repair and Regeneration; S32-S39; 15 pages; (Author Manuscript); Sep. 2007.

Zhu et al.; The female, red duroc pig as an animal model of hypertrophic scarring and the potential role of the cones of skin; Burns; 29(7); pp. 649-664; Nov. 2003.

\* cited by examiner a b

FIG. 7A
FIG. 7B
Porcine deep wound
FIG. 7C
Intact Pig skin
FIG. 7D
Wounded (depth= 0.06 in.)
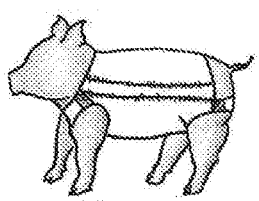
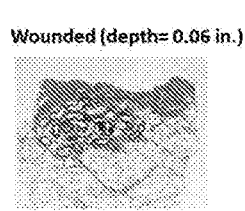
FIG. 7E
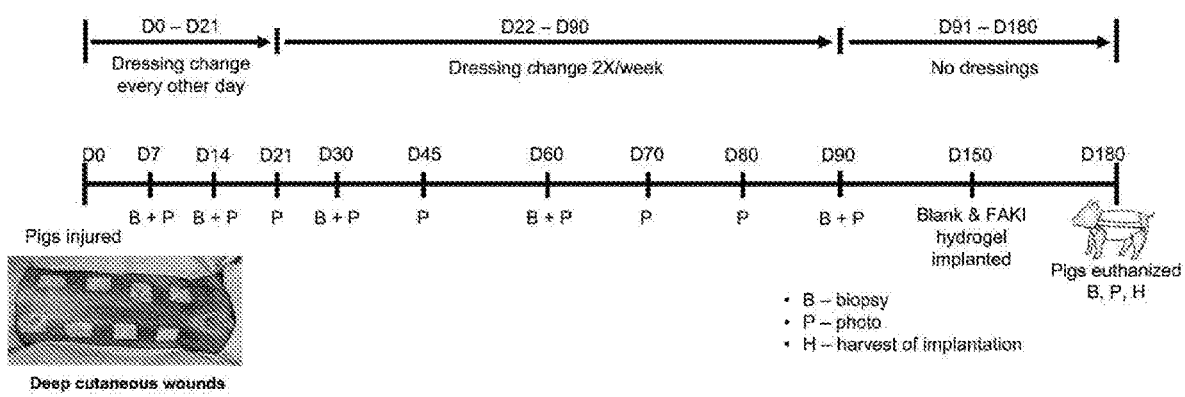

FIG. 11A
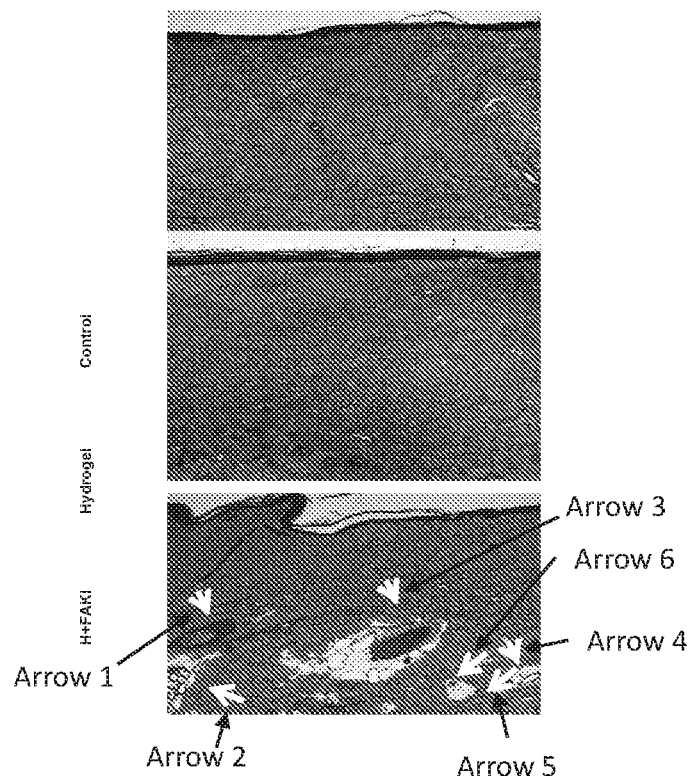
FIG. 11B
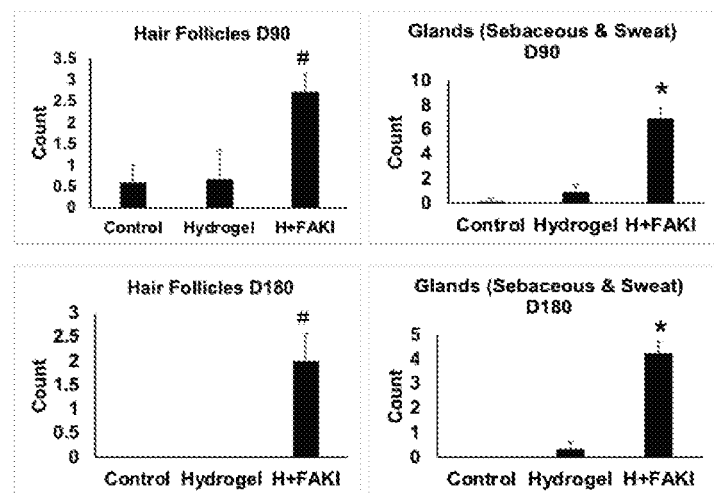
FIG. 11C

FIG. 12A
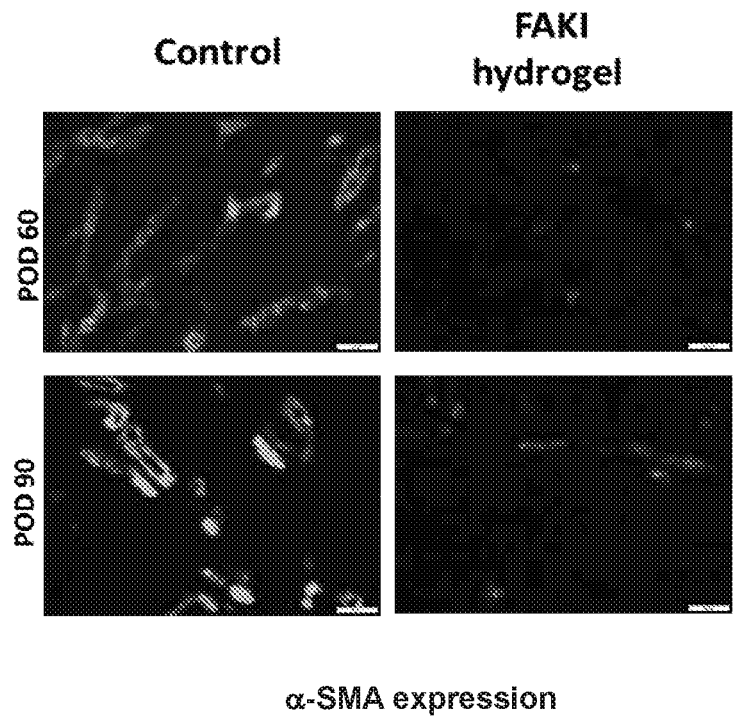
α-SMA expression
FIG. 12B
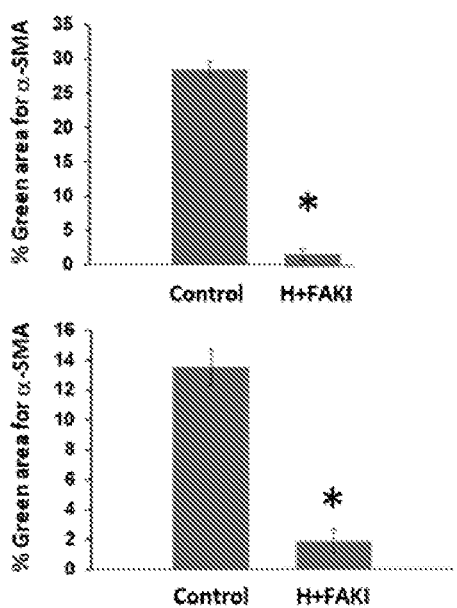
FIG. 12C

FIG. 13A
FIG. 13B
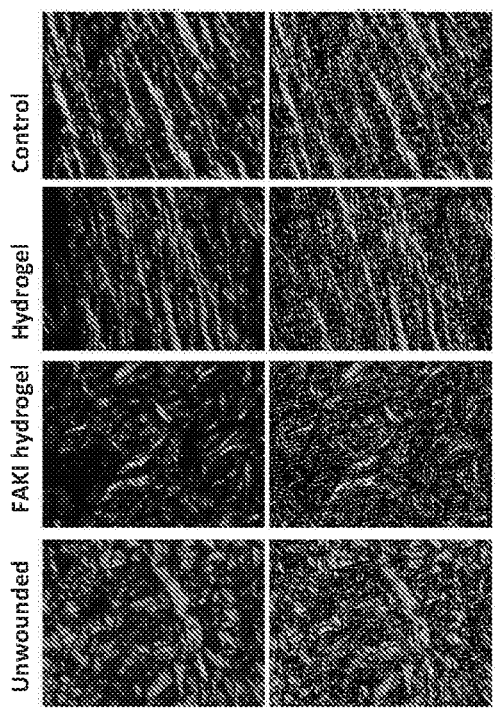
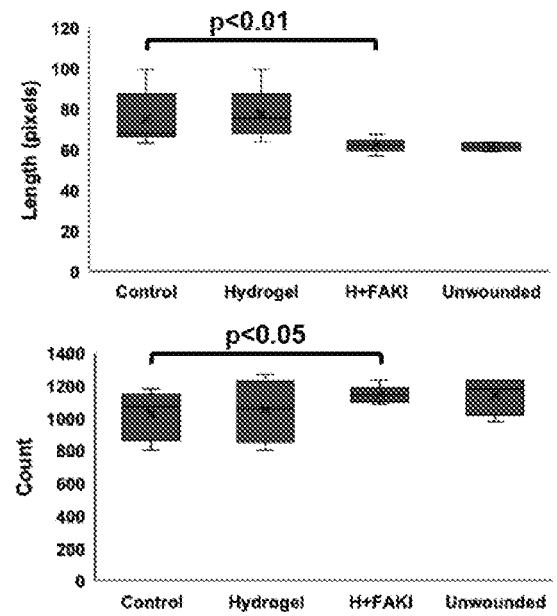
FIG. 13C
FIG. 14
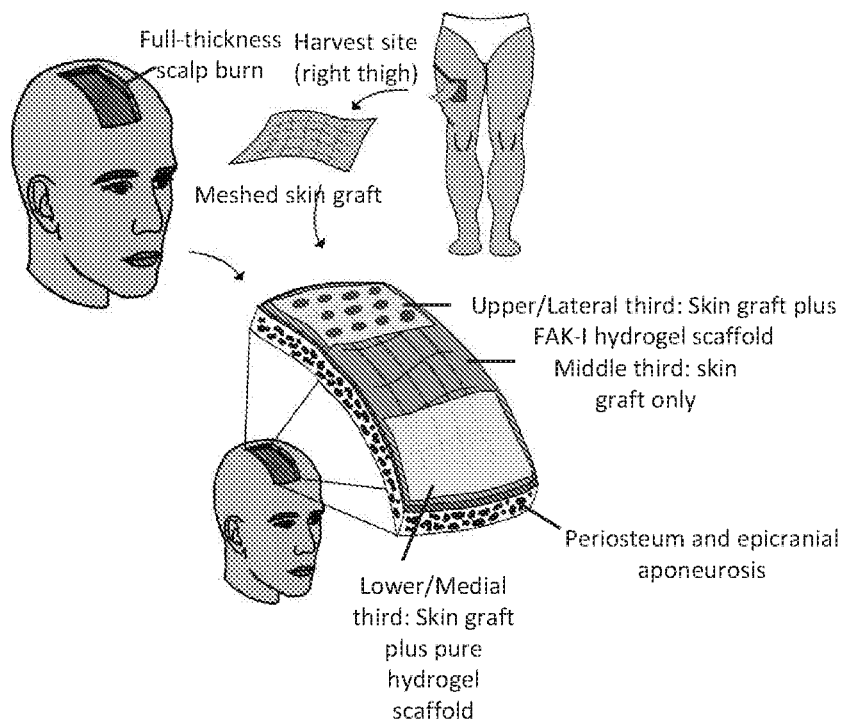

CONTROLLED HYDROGEL DELIVERY OF FOCAL ADHESION KINASE INHIBITOR FOR DECREASED SCAR FORMATION

CROSS REFERENCE TO RELATED APPLICATIONS

This application claims the benefit of U.S. Provisional Patent Application No. 62/672,513, filed May 16, 2018, and U.S. Provisional Patent Application No. 62/848,515, filed May 15, 2019, each of which is herein incorporated by reference in its entirety.

STATEMENT AS TO FEDERALLY SPONSORED RESEARCH

This invention was made with Government support under Grants No. W81XWH-13-2-0052 and W81XWH-13-2-0054 awarded by the Department of Defense, Grant No. DE026914 awarded by the National Institutes of Health and Grant No. WFUHS441011SR01 awarded by Armed Forces Institute of Regenerative Medicine (AFIRM DoD). The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure is related generally to treating wounds and promoting tissue healing of wounds. In particular, described herein are compositions including a porous scaffold and a focal adhesion kinase (FAK) inhibitor, and methods of making and using such compositions.

BACKGROUND

Cutaneous scar formation represents a significant medical burden with billions of dollars spent annually on wound and scar treatments. Unfortunately, current strategies to prevent and/or treat scarring have largely been unsuccessful due to our lack of comprehensive understanding of the underlying pathophysiology. Recent reports from our laboratory have demonstrated the importance of mechanical stress in modulating biological processes associated with hypertrophic scar (HTS) formation. Sustained mechanical load applied to healing incisions resulted in fibrotic responses and HTS formation in these studies.

A key modulator of this process is focal adhesion kinase (FAK), a cytoplasmic tyrosine kinase, which plays a central role in transducing mechanical signals to elicit fibrotic responses. The Integrin-FAK pathway also mediates tumor progression and metastasis in various malignancies. Pharmacological inhibitors of FAK have been emerging as anti-cancer chemotherapeutics in preclinical and clinical studies. Cancer and hypertrophic scars share similarities in that exuberant fibroproliferative and extracellular matrix-remodeling events underlie their pathogenesis.

In this context, FAK is also an attractive and potentially promising target for anti-scar therapies. Fibroblast specific deletion of FAK in knockout mice displayed substantially reduced inflammation and fibrosis in an incisional HTS model. Loss of keratinocyte-restricted FAK, however, was associated with increased dermal proteolysis presumably contributing to wound chronicity. In our previous study, inhibition of FAK with a small molecule inhibitor by local subcutaneous injection abrogated the local inflammatory responses and decreased scar development in a HTS mouse model.

In preclinical and clinical studies, off-loading of mechanical strain using stress-shielding devices in incisional and excisional wounds has proven to be effective in inhibiting scar development in large animals and humans. Approaches to physically reduce mechanical strain, however, are not applicable to large areas of wounds resulting from extensive burns, traumatic blast injuries, or excisional skin surgeries.

Hence, there is a critical need for topical biomaterial-based dressings that allow for targeted and controlled release of pharmacological inhibitors. Methods of improving healing, particularly for amelioration of scarring, are of great interest. The present invention addresses this.

SUMMARY OF THE DISCLOSURE

The present invention relates to treating wounds and promoting tissue healing of wounds. In particular, described herein are compositions including a porous scaffold and a focal adhesion kinase (FAK) inhibitor, and methods of making and using such compositions.

One aspect of the invention provides a composition for promoting tissue healing. In some embodiments, the composition may include a porous scaffold. In some embodiments, the composition may include focal adhesion kinase (FAK) inhibitor disposed in pores of the scaffold. In some embodiments, the composition is configured to deliver a dose of FAK inhibitor effective to promote tissue healing at a controlled rate during a treatment time.

In some embodiments, the porous scaffold includes a hydrogel film. In some embodiments, the porous scaffold includes a pullulan-collagen hydrogel.

In some embodiments, the FAK inhibitor includes VS-6062 (PF-562271) or a benzenesulfonate salt of PF-562271. In some embodiments, the composition includes from about 1 µg/cm$^2$ to about 500 µg/cm$^2$ of the FAK inhibitor. In some embodiments, the composition includes from about 40 µg/cm$^2$ to about 200 µg/cm$^2$ of the FAK inhibitor.

In some embodiments, the composition is configured for sustained release of the FAK inhibitor disposed in pores of the scaffold. In some embodiments, the composition is configured for sustained release of the FAK inhibitor disposed in pores of the scaffold over a period of up to about 96 hours.

In some embodiments, the composition is fabricated by molecular imprinting of the FAK inhibitor during formation of the porous scaffold. In some embodiments, the composition is fabricated for rapid release of FAK inhibitor. In some embodiments, the composition includes FAK inhibitor on a delivery surface of the composition. In some embodiments, the composition is further configured for rapid release of FAK inhibitor from the delivery surface of the composition. In some embodiments, the composition is configured for rapid release of FAK inhibitor from a delivery surface of the composition within about 24 hours.

In some embodiments, the composition is tailored to release substantially all of the FAK inhibitor during the treatment time. In some embodiments, the composition is tailored to release from about 30% of the FAKI inhibitor to about 75% of the FAK inhibitor during the treatment time.

In some embodiments, the composition includes a plurality of layers wherein one or more layers is fabricated for sustained release of the FAK inhibitor and one or more layers is fabricated for rapid release of the FAK inhibitor. In some embodiments, the composition includes a layer configured for both sustained release of the FAK inhibitor and rapid release of the FAK inhibitor.

In some embodiments, the composition is configured to deliver during the treatment time a dose of the FAK inhibitor effective to reduce scarring of the tissue. In some embodiments, the composition is configured to deliver during the treatment time a dose of the FAK inhibitor effective to promote hair growth in the tissue.

In some embodiments, the composition is configured as a wound dressing.

Yet another aspect of the invention provides a method for promoting tissue healing. In some embodiments, the method includes placing on a surface of the tissue a composition comprising a porous scaffold and a focal adhesion kinase (FAK) inhibitor fabricated for controlled release disposed in pores of the scaffold. In some embodiments, the method includes delivering to the surface of the tissue a dose of the FAK inhibitor effective to promote tissue healing at a controlled rate during a treatment time.

In some embodiments, the porous scaffold includes a hydrogel film. In some embodiments, the hydrogel comprises a pullulan-collagen hydrogel.

In some embodiments, the method further includes reducing scarring of tissue. In some embodiments, the method further includes promoting hair growth in the tissue.

In some embodiments, the composition is configured as a wound dressing.

In some embodiments, FAK inhibitor is disposed on a delivery surface of the composition. In some embodiments, the controlled rate includes a rapid release rate and a sustained release rate. In some embodiments, the delivering step of the method includes delivering to the surface of the tissue the dose of the FAK inhibitor within about 24 hours after the placing step. In some embodiments, the dose of the FAK inhibitor is delivered to the tissue surface over a period of up to about 96 hours.

In some embodiments, the method further includes removing the composition from the tissue surface. In some embodiments, the method includes repeating the placing and delivering steps at least 3 times. In some embodiments, the method further includes repeating the placing and delivering steps at least 10 times.

In some embodiments, the FAK inhibitor is VS-6062 (PF-562271) or a benzenesulfonate salt of PF-562271.

In some embodiments, the method includes delivering to the tissue from about 30% of the FAKI inhibitor in the composition to about 75% of the FAK inhibitor in the composition.

Yet another aspect of the invention provides method of manufacturing a composition with a porous scaffold for treating a wound. In some embodiments, the method includes the step of forming a mixture comprising a focal adhesion kinase (FAK) inhibitor, pullulan, collagen, and a porogen. In some embodiments, the method includes the step of removing the porogen and/or dehydrating the mixture to thereby create a composition with a porous scaffold having focal adhesion kinase (FAK) inhibitor disposed in pores of the scaffold fabricated for controlled drug release.

In some embodiments, the porous scaffold includes a hydrogel. In some embodiments, the porous scaffold includes a pullulan and collagen hydrogel.

In some embodiments, the method includes the step of placing FAK inhibitor on a surface of the composition.

In some embodiments, the method includes the step of cross-linking the pullulan. In some embodiments, the method includes the step of cross-linking the pullulan with sodium trimetaphosphate (STMP) and/or sodium tripolyphosphate (STPP).

In some embodiments, the method includes the step of crystalizing the porogen prior to the removing step.

In some embodiments, the composition includes a non-uniform distribution of FAK inhibitor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

(FIG. 1A) Schematic of molecular imprinting of FAKI into pullulan-collagen hydrogel scaffold. (FIG. 1B) Digital photographs of dry pullulan-collagen hydrogel (up) and swollen hydrogel in PBS after water absorption (down). (FIG. 1C) In vitro release profiles of FAKI from pullulan-collagen hydrogels containing 50 μg FAKI prepared by molecular imprinting blue) and surface incorporation (red). N=three experiments per indicated time-point.

(FIG. 2A) Digital photographs of splinted full-thickness excisional wounds treated with or without FAKI hydrogel. (FIG. 2B) Quantification of wound closure days and time-dependent change of wound area following injury. (FIG. 2C) Groups: no scaffold or FAKI (Control), pullulan-collagen hydrogel (Hydrogel), and FAKI-releasing pullulan-collagen hydrogel (H+FAKI). N=8 wounds for each condition. Statistical differences are at *$p<0.05$ vs. Control for each time-point indicated.

(FIG. 3A) Representative H&E and Masson's Trichrome staining images of healed wounds. (FIG. 3B) Quantification of blue area in Masson's Trichrome staining images of healed wounds in Control, Hydrogel, and H+FAKI on Day 17 post-injury. H&E: cytoplasm and extracellular matrix (red) and cell nuclei (black). Masson's Trichrome staining: collagen (blue), cytoplasm and muscle (red), and cell nuclei (black). Scale bar=100 μm; (FIG. 3C) Immunofluorescence staining of α-SMA and (FIG. 3D) quantification of green area in Control, Hydrogel, and H+FAKI on Day 17 post-injury. α-SMA (green) and cell nuclei (blue). Scale bar=50 μm. (FIG. 3E) Representative western blotting images and (FIG. 3F) quantification of FAK and p-FAK of wound lysates on Day 10 post-injury. N=8 wounds for each condition. (FIG. 3G) Immunofluorescence staining of p-Akt and (FIG. 3H) quantification of green area in Control, Hydrogel, and H+FAKI on Day 17 post-injury. p-Akt (green) and cell nuclei (blue). Scale bar=100 μm. For all analyses, statistical differences are at *$p<0.05$ Control vs. H+FAKI, $\Delta p<0.05$ Hydrogel vs. H+FAKI, and #$p<0.05$ Control vs. Hydrogel.

and ultimate tensile stress (MPa) (FIG. 4B) in Control, Hydrogel, H+FAKI groups at 3 weeks post-injury. N=8 wounds for each condition. For all analyses, statistical differences are at *p<0.05 Control vs. H+FAKI and #p<0.05 Control vs. Hydrogel.

FIG. 5A-FIG. 5D show improved wound healing and attenuated myofibroblast deposition with FAKI treatment in a contact burn wound model. (FIG. 5A) Digital photographs of full-thickness contact burn wounds treated with and without FAKI hydrogel. (FIG. 5B) Quantification of time-dependent change of wound area following injury. (FIG. 5C) Immunofluorescence staining of α-SMA and (FIG. 5D) quantification of green area in Control, Hydrogel, and H+FAKI on Day 24 post-debridement. N=7 wounds for each condition. Scale bar=250 μm. For all analyses, statistical differences are at *p<0.05 Control vs. H+FAKI and Δp<0.05 Hydrogel vs. H+FAKI.

FIG. 6A-FIG. 6B show local subcutaneous injection of FAKI reduces scar formation of murine incisions. (FIG. 6A) Masson's Trichrome staining of murine dorsal incisions treated with increasing concentrations of FAKI dissolved in 10% DMSO showed reduced scar lesions at 15 and 75 μM FAKI. N=5 wounds for each condition. Scale bar=100 μm. Animals did not survive more than 2 days with 150 μM FAKI injection. (FIG. 6B) Quantification of scar area (dashed lines) for each condition. Statistical differences are at *p<0.05 vs. Control.

FIG. 7A-FIG. 7E shows the setup and timeline used for analyzing the effects of topical treatment of FAKI applied in a hydrogel device to deep cutaneous wounds in a red Duroc pig model to as described herein. FIG. 7A shows the region used for testing. FIG. 7B shows an example of a porcine deep wound with the removed skin. FIG. 7C shows a cross sectional view of intact pig skin. FIG. 7D shows a cross-sectional view of wound pig skin with a wounded depth of 0.06 inches (in). FIG. 7E shows the timeline from the day of injury (D0) to 180 postoperative days (D180).

Figure 8A:
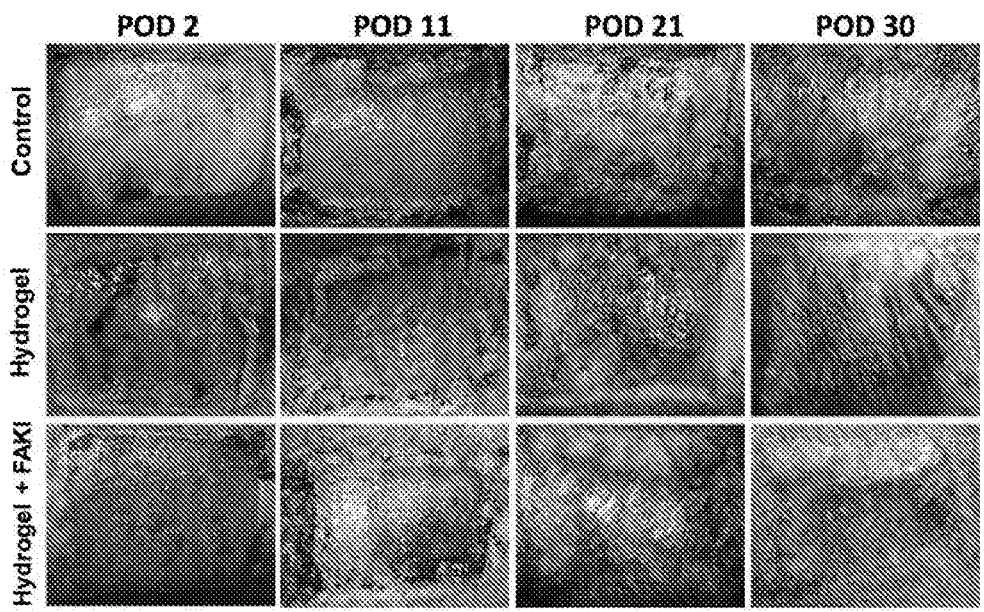
Figure 8B:
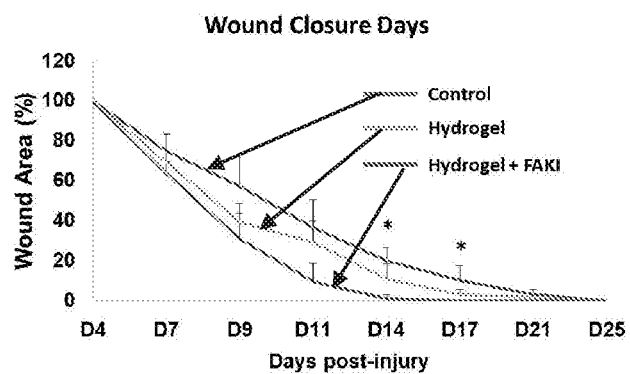
Figure 8C:
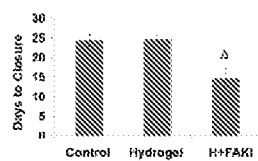

FIG. 8A-FIG. 8C show that topically treating deep cutaneous wounds in Duroc pigs with FAKI hydrogel accelerates wound healing. N=8 wounds for each condition. Initial wound size=25 cm$^2$. FIG. 8A shows photographs of the wounds taken from postoperative day (POD) 2 to POD 30. Wounds appear more healed after POD 11 through POD 21 and POD 30. The wound area was measured over time and FIG. 8B shows the results over time for FAKI hydrogel treated wounds vs hydrogel treated wounds or untreated wounds. The wound treated with FAKI in a hydrogel device shows accelerated healing at POD 21, and POD 30 than do wounds left untreated (control) or wounds treated with hydrogel alone. By POD 14, FAKI hydrogel treated wounds had about completely closed while untreated (control) wounds still had 20% open wounds, a statistically significant difference (indicated with a *). By POD 17, FAKI hydrogel treated wounds had completely closed while untreated (control) wounds still had about 10% open wounds, a statistically significant difference (indicated with a * in FIG. 8B). FIG. 8C shows that untreated wounds or wounds treated with hydrogel alone take 25 days to fully close, while wounds treated with FAKI in a hydrogel device are closed by POD 14, a statistically significant result.

Figure 9A:
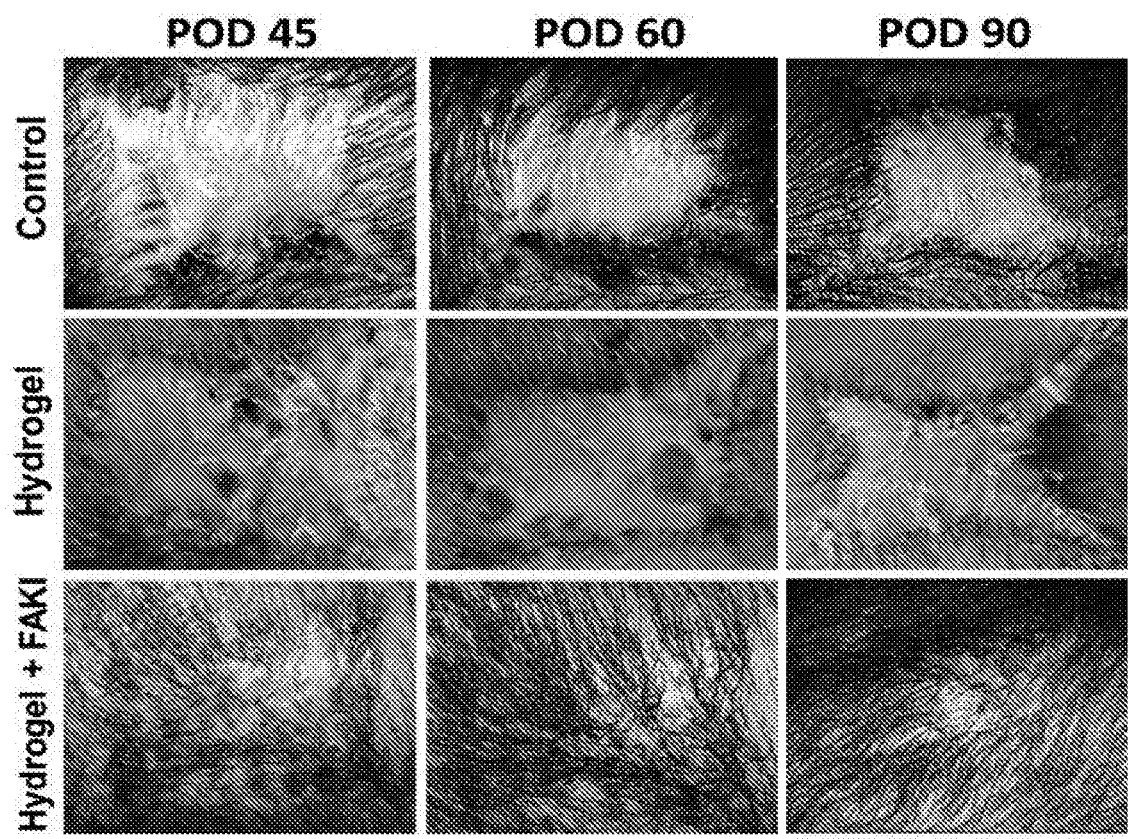
Figure 9B:
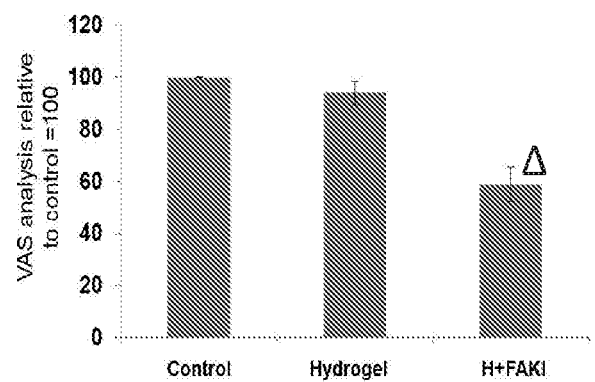

FIG. 9A-FIG. 9B show that topically treating deep cutaneous wounds in Duroc pigs with FAKI hydrogel significantly improves scar appearance. FIG. 9A shows photographs of wounds taken from postoperative day (POD) 45 to postoperative day 90. The wound treated with FAKI in a hydrogel device (bottom row) shows noticeably improved appearance from postoperative day 45 to postoperative day 90 compared with wounds left untreated (top row) or wounds treated with hydrogel alone (middle row). Additionally, the wound treated with FAKI in the hydrogel device shows noticeably more hair in the wound area. FIG. 9B shows that wounds treated with topical application of FAKI in a hydrogel device have improved appearance at 90 days when assessed by blinded scar experts. Four blinded scar experts assessed the scars using Visual Analog Scale (VAS). The untreated control was scored at 100, treatment with hydrogel alone at 95, and treatment with FAKI in a hydrogel device showed a significantly improved score of 60: treatment with FAKI in a hydrogel device has a Visual Analog Scale (VAS) scores were assessed by four blinded scar experts (*p<0.001).

Figure 10A:
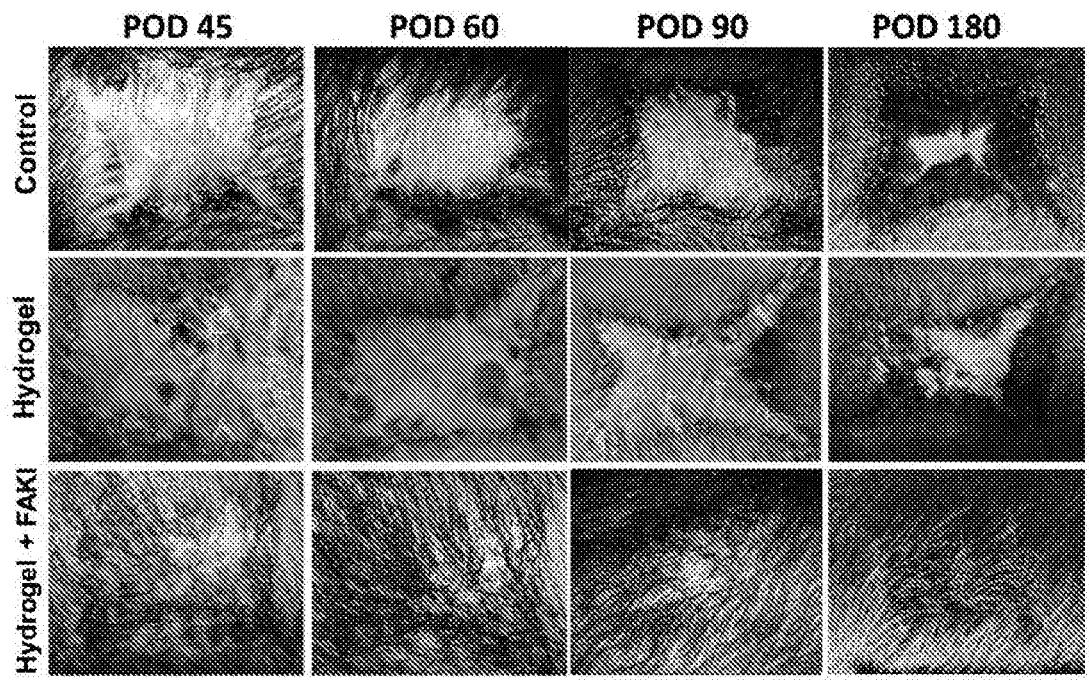
Figure 10B:
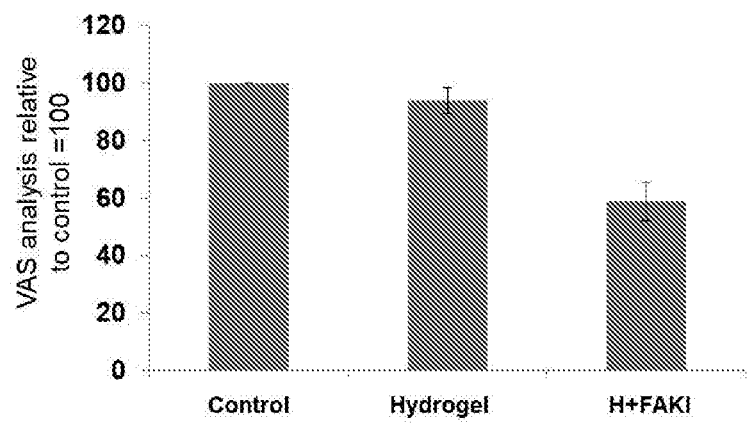

FIG. 10A-FIG. 10B show that topically treating deep cutaneous wounds in Duroc pigs with FAKI hydrogel improves scar appearance and improved scar appearance persists at 6 months. FIG. 10A shows photographs of wounds taken from postoperative day (POD) 45 to POD 180 (6 months). The wound treated with FAKI in a hydrogel device shows noticeably improved appearance from post-operative day 45 to postoperative day 180 compared with wounds left untreated or wounds treated with hydrogel alone. Additionally, the wound treated with FAKI in a hydrogel device shows hair in the wound area. FIG. 10B shows that wounds treated with topical application of FAKI in a hydrogel device have improved appearance when assessed by blinded scar experts. Four blinded scar experts assessed the scars using Visual Analog Scale (VAS). The untreated control was scored at 100, treatment with hydrogel alone at 95, and treatment with FAKI in a hydrogel device showed a significantly improved score of 60: treatment with FAKI hydrogel has a $^ΔP<0.0001$ Control vs. H+FAKI.

FIG. 11A-FIG. 11C show that topically treating deep cutaneous wounds with FAKI hydrogel restores hair follicles and skin appendages. FIG. 11A shows Trichrome staining of FAKI hydrogel treated wounds (bottom) row, compared with untreated wounds (top row) and wounds treated with hydrogel alone (middle row) at postoperative day 90. Arrow 1 points to a hair follicle. Arrow 3 points to a hair follicle with surrounding glandular structures. Arrow 2 and Arrows 4-6 point to cutaneous glands (sweat and sebaceous glands). FIG. 11B-FIG. 11C shows results from counting the number of hair follicles (left graph) and sebaceous and sweat glands (right graph). Untreated wounds are on the left side of each graph, wounds treated with hydrogel alone are in the middle, and wounds treated with FAKI hydrogel are on the right. At postoperative day 90, FAKI hydrogel treated wounds had significantly more hair follicles with an average of about 2.7 hair follicles, while wounds treated with hydrogel alone had an average of about 0.7 hair follicles and untreated wounds had about 0.6 hair follicles.

FIG. 12A-FIG. 12C show that topically treating deep cutaneous wounds with FAKI hydrogel blocks myofibroblast recruitment and activation. FIG. 12A shows results from staining control and FAKI hydrogel treated wounds for α-smooth muscle actin. FIG. 12B-FIG. 12C show results from blinded observers quantifying the amount of α-smooth muscle actin within randomly selected regions within scar lesions for POD 60 (FIG. 12B) and POD90 (FIG. 12C). The FAKI hydrogel treated wounds showed significantly less α-smooth muscle actin compared with controls (*p<0.001).

FIG. 13A-FIG. 13C show that FAKI hydrogel treatment results in better dermal architecture that resembles unwounded normal skin. The left panels of FIG. 13A show dermal collagen staining against a dark background. The right panels of FIG. 13A show the automated collagen fiber segmentations that are extracted by the CT-FIRE quantitative fiber analysis algorithm. Fibers in different colors represent individual collagen fibers with different fiber metrics generated by computational extraction. FIG. 13B shows length (in pixels) of collagen fibrils such as those shown in FIG. 13A. The mean and median size of the collagen fibers is significantly smaller in the FAKI hydrogel compared with the untreated control. FIG. 13C shows the absolute counts of the individual collagen fibers of certain type per image that were analyzed by CT-FIRE algorithm.

FIG. 14 shows a device as described herein for promoting tissue healing and reducing scarring. The device includes a skin graft with a FAKI hydrogel scaffold.

Figure 15A:
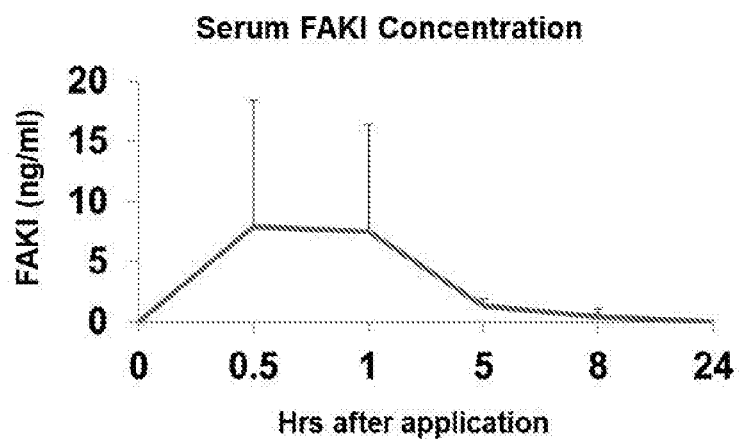
Figure 15B:
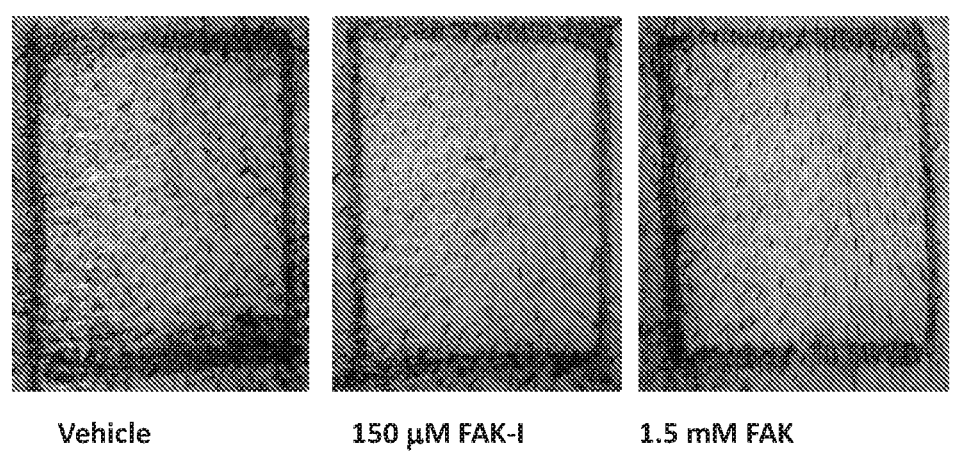

FIGS. 15A-FIG. 15B show safety of a FAKI hydrogel delivered locally to skin. FIG. 15A shows insignificant levels of systemic absorption after local delivery of FAK hydrogels. FIG. 15B shows daily application of even high concentration of FAKI solution to unwounded skin did not result in irritation or sensitization of skin.

DETAILED DESCRIPTION

Compositions, and devices and methods using the compositions, are provided for promoting tissue healing, such as ameliorating the formation of scars at a wound site and forming new hair and skin appendages. The compositions include a scaffold, e.g., a porous scaffold and an effective dose of an inhibitor of focal adhesion kinase (FAK) activity fabricated for controlled drug release. The scaffold may be configured to deliver to a delivery surface a dose of the FAK inhibitor effective to promote tissue healing at a controlled rate during a treatment time. In some examples, a composition is configured to or brought into contact with the skin at the site of a wound, for a period of time sufficient to promote tissue healing and/or reduce scarring, e.g., relative to a wound not treated by the methods of the invention. Aspects of the disclosure provide methods for treating an injury, re-epithelialization of a wound, preventing or reducing scarring during healing of a wound of the skin, forming new hair and skin appendages, wherein an effective dose of the FAK inhibitor is brought into contact with the wound. In some embodiments, the subject is a human subject. In some embodiments, the injury is a cut, which can be an incision of the epidermis, a burn, a wound which may be open or closed, and the like. Examples of open wounds include, but are not limited to, an incision, a laceration, an abrasion, a puncture wound, a penetration wound, a gunshot wound, and/or a stabbing wound. In some embodiments, the porous scaffold is a porous hydrogel, such as a pullulan-collagen hydrogel.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

Definitions

Focal adhesion kinase (FAK), also known as cytoplasmic protein-tyrosine kinase (PTK2), is a cytosolic protein tyrosine kinase concentrated in the focal adhesions that form among cells attaching to extracellular matrix constituents (see Andre et al. (1993) Biochem. Biophys. Res. Commun. 190: 140-147). FAK is a highly conserved, non-receptor tyrosine kinase of 125 kD, which is recruited as a participant in focal adhesion dynamics between cells, and has a role in motility and cell survival. FAK is phosphorylated in response to integrin engagement, growth factor stimulation, and the action of mitogenic neuropeptides. A carboxy-terminal region of one hundred and fifty-nine amino acids, the focal adhesion targeting domain (FAT), has been shown to be responsible for targeting FAK to focal adhesions. Paxillin, a focal adhesion adaptor protein binds to FAK at a carboxy-terminal domain that overlaps the FAT domain. Between the amino and the carboxy regions lies the catalytic domain. Phosphorylation of the activation loop within this kinase domain is important for the kinase activity of FAK.

Exemplary inhibitors of FAK are provided in Table 1 below. An inhibitor of interest is PF-562271, which is a potent, ATP-competitive, selective and reversible inhibitor of FAK with $IC_{50}$ of 1.5 nM. Also of interest us PF-00562271, which is the benzenesulfonate salt of PF-562271.

Inhibitors of FAK. A number of FAK inhibitors are known and used in the art.

TABLE 1

| Inhibitor Name | FAK | Other Targets |
|---|---|---|
| PF-562271 | ++++ | CDK2/CyclinE,CDK3/CyclinE,CKD1/CyclinB |
| PF-573228 | + | |

TABLE 1-continued

| Inhibitor Name | FAK | Other Targets |
|---|---|---|
| TAE226 (NVP-TAE226) | ++ | Insulin Receptor, IGF-1R, c-Met |
| PF-03814735 | + | Aurora A, Aurora B, FLT1 |
| PF-562271 HCl | ++++ | CDK2/CyclinE, CDK3/CyclinE, CKD1/CyclinB |
| GSK2256098 | ++++ | |
| PF-431396 | ++ | |

TABLE 1-continued

| Inhibitor Name | FAK | Other Targets |
|---|---|---|
| PND-1186 (VS-4718) | ++++ | |
| Defactinib (VS-6063, PF-04554878) | ✓ | |
| Solanesol (Nonaisoprenol) | ✓ | |

Porous scaffold A structure having pores or openings. The structure may include natural and/or synthetic polymers or copolymers. Examples of materials suitable for forming a porous scaffold include acrylic polymers, cellulose, chitosan, collagen, cellulosic polymers, gelatin, gums, poly(lactic-co-glycolic acid) (PLGA), poly(L-lactide)/poly(ε-caprolactone), polyvinyl group polymers, pullulan, and other polysaccharides. The pores may be extend from a first surface of the scaffold to a second surface, extending all the way though the scaffold or may be closed on at least a first surface. Pores may have interconnected small voids. Pores may be irregular or regular. Irregular pores may be irregular in a size aspect (e.g., diameter) or a length aspect. Regular pores may be similar to one another in size, shape, or distribution. Pores (especially regular pores) may be formed using a porogen, or a mass of particles that are dissolved away after the scaffold has set. Examples of porogens that can be utilized include potassium chloride, sodium chloride, sucrose, glucose, lactose, sorbitol, xylitol, polyethylene glycol, polyvinylpyrrollidone, and polyvinyl alcohol. Pores (especially regular pores) may be formed by laser drilling or 3D printing. Porosity may be optimized for retaining and releasing a drug (e.g., FAK inhibitor) for a desired time or at a desired rate. Porosity may be optimized for retaining and releasing a drug (e.g., FAK inhibitor) to a delivery surface on the porous scaffold. Porosity may be optimized for retaining and releasing a drug (e.g., FAK inhibitor) from a delivery surface on the porous scaffold to a tissue surface. Porous scaffolds may be hydrogels and hold, or be configured to hold a fluid such as water.

Hydrogel A wound dressing is a material applied to a wound or incision for covering and protecting a wound. For example, carbohydrate-based hydrogels may be fabricated using pullulan and collagen under conditions that provide for cross-linking and pore formation. Collagen can be added to a mixture of pullulan, cross-linking agent and pore forming agent (porogen), where the collagen is provided at a concentration of at least about 1%, and not more than about 12.5% relative to the weight of the pullulan. Collagen may be provided at a concentration of about 1%, about 2.5%, about 5%, about 7.5%, about 10%, usually at a concentration of from about 2.5% to about 10%, and may be from about 4% to about 6%, which collagen is typically a fibrous collagen, e.g., Type I, II, III, etc. Cross-linking agents of interest include sodium trimetaphosphate (STMP) or a combination of sodium trimetaphosphate and sodium tripolyphosphate (STMP/STPP), e.g., at a wt/wt ratio of from about 1:5, about 1:2, about 1:1, about 1:2 with pullulan. Porogens of interest for in-gel crystallization include any suitable porogen, such as a salt, e.g., KCl, e.g., at a wt/wt ratio of from about 1:5, about 1:2, about 1:1, about 1:2 with pullulan. For molecular imprinting, the FAK inhibitor may be added to a concentration of from about 100 μg/ml to about 100 mg/ml in the mixture, and may be from about 1 mg/ml to about 10 mg/ml. For surface incorporation, a solution of FAK inhibitor in a suitable excipient, e.g., an aqueous solution, ethanol, etc. may be applied to the surface after the gel is formed.

The composition can be poured and compressed to form sheets. Preferred thickness is at least about 1 mm and not more than about 5 mm, usually not more than about 3 mm, and may be from about 1.75 to 2.5 mm, e.g., about 2 mm thick.

Pores can be formed in the hydrogel through rapid desiccation of swollen hydrogels by phase inversion. Thus, some embodiments include the step of dehydrating the mixture or swollen hydrogel. Dehydration results in localized supersaturation and crystallization of the porogen. Pullulan and collagen are forced to organize around the crystals in an interconnected network which results in reticular scaffold formation following KCl dissolution. Thus, some embodiments include the step of removing the porogen. The addition of a porogen augments hydrogel viscoelasticity. The improved scaffold porosity allows for greater fluid absorption, a higher water to polymer ratio, and more effective hydrogel behavior.

The films may be stored in a dried state, and are readily rehydrated in any suitable aqueous medium. The aqueous nature of hydrogel substrates provides an ideal environment for cellular growth and sustainability in wound healing.

Mechanical features of a hydrogel include average pore size and scaffold porosity. For pullulan-collagen hydrogels, both variables vary with the concentration of collagen that is present in the hydrogel. For a hydrogel comprising 5% collagen, the average pore size will usually range from about 25 µm to about 50 µm, from about 30 µm to about 40 µm, and may be about 35 µm. For a hydrogel comprising 10% collagen the average pore size will usually range from about 10 µm to about 25 µm, from about 12 µm to about 18 µm, and may be about 15 µm. One of skill in the art will readily determine suitable hydrogels at other collagen concentrations. The scaffold porosity will usually range from about 50% to about 85%, and may range from about 70% to about 75%, and will decrease with increasing concentrations of collagen.

Pullulan. A polysaccharide polymer originally from the fungus *Aureobasidium pullulans*. It is a linear homopolysaccharide having alpha-(1-6) linked maltotriose units and exhibits water retention capabilities in a hydrogel state which makes it an ideal therapeutic vehicle for both cells and biomolecules. Additionally, pullulan contains multiple functional groups that permit crosslinking and delivery of genetic material and therapeutic cytokines. Furthermore, pullulan-based scaffolds have been shown to enhance both endothelial cell and smooth muscle cell behavior in vitro.

Collagen. As used herein the term "collagen" refers to compositions in which at least about 50%, at least about 60%, at least about 70%, at least about 80%, at least about 90%, at least about 95% or more of the protein present is collagen in a triple helical configuration. Collagens are widely found in vertebrate species, and have been sequenced for many different species. Due to the high degree of sequence similarity between species, collagen from different species can be used for biomedical purposes, e.g., between mammalian species. Typical commercial animal sources include the bovine Achilles tendon, calfskin and the bones of cattle. In some embodiments the collagen used in the preparation of the oriented thin film is Type I, Type II or Type III collagen, and is derived from any convenient source, e.g., bovine, porcine, etc., usually a mammalian source.

Collagen has a triple-stranded ropelike coiled structure. The major collagen of skin, tendon, and bone is collagen I, containing 2 alpha-1 polypeptide chains and 1 alpha-2 chain. The collagen of cartilage contains only 1 type of polypeptide chain, alpha-1. The fetus also contains collagen of distinctive structure. The genes for types I, II, and III collagens, the interstitial collagens, exhibit an unusual and characteristic structure of a large number of relatively small exons (54 and 108 bp) at evolutionarily conserved positions along the length of the triple helical gly-X-Y portion.

Types of collagen include I (COL1A1, COL1A2); II (COL2A1); III (COL3A1); IV (COL4A1, COL4A2, COL4A3, COL4A4, COL4A5, COL4A6); V (COL5A1, COL5A2, COL5A3); VI (COL6A1, COL6A2, COL6A3); VII (COL7A1); VIII (COL8A1, COL8A2); IX (COL9A1, COL9A2, COL9A3); X (COL10A1); XI (COL11A1, COL11A2); XII (COL12A1); XIII (COL13A1); XIV (COL14A1); XV (COL15A1); XVI (COL16A1); XVII (COL17A1); XVIII (COL18A1); XIX (COL19A1); XX (COL20A1); XXI (COL21A1); XXII (COL22A1); XXIII (COL23A1); XXIV (COL24A1); XXV (COL25A1); XXVII (COL27A1); XXVIII (COL28A1). It will be understood by one of skill in the art that other collagens, including mammalian collagens, e.g., bovine, porcine, equine, etc. collagen, are equally suitable for the methods of the invention. Additionally or instead, collagen may also be made synthetically.

Supports. A variety of solid supports or substrates may be used with the porous scaffold (hydrogel), including deformable supports. By deformable is meant that the shape of the support can be changed into something else. Examples of deformable solid supports include polyacrylamide, nylon, nitrocellulose, polypropylene, polyester films, such as polyethylene terephthalate; PDMS (polydimethylsiloxane); etc. as known in the art for the fabrication of wound dressings.

Wound dressings. A wound dressing is a material applied to a wound or incision for covering and protecting a wound. For example, porous substrates, such as hydrogels for promoting tissue healing (e.g., to ameliorate the formation of a scar and/or keloid, at a wound site) are one type of wound dressing. In general, the porous substrates, such as hydrogels are configured to be removably secured to a skin or other tissue surface, may include one or more active agents (drugs). In other examples, a wound dressing or part of a wound dressing may be biodegradable. The hydrogel may have any suitable shape or size.

Additional criteria for biologically active wound dressings may include one or more of: rapid adherence to the wound soon after placement; proper vapor transmission to control evaporative fluid loss from the wound and to avoid the collection of exudate between the wound and the dressing material. Biologically active wound dressings may act as skin substitutes and may act as one or more to: as a barrier to microorganisms, limit the growth of microorganisms already present in the wound, be flexible, durable and resistant to tearing. The skin substitute generally exhibits tissue compatibility, that is, it should not provoke inflammation or foreign body reaction in the wound which may lead to the formation of granulation tissue. An inner surface structure of a hydrogel thin film as described herein may be provided that permits ingrowth of fibro-vascular tissue. An outer surface structure may be provided to minimize fluid transmission and promote epithelialization.

In some examples, FAKI alone or a FAKI hydrogel (e.g., pullulan/collagen hydrogel) may be part of a graft. The term "graft" generally refers to a piece of skin removed from one part of a body and then moved to (and attached) to a new site on the same (or a different) body. FIG. 14 shows an example of a FAKI porous scaffold skin graft. The patient has a full thickness scalp burn. A piece of skin is harvested from a harvest site (the right thigh, in this case) and layered with (overlaid, in this case) with a porous scaffold with FAKI. In this example for illustrative purposes, the graft also includes control regions, including a region that is not overlaid with a porous substrate with FAKI and a region that is overlaid with a porous substrate without FAKI though a graft for transplanting would more generally be layered largely along most or all of the side with hydrogel with FAKI.

The term "wound" generally refers to both open and closed wounds, as described below. A wound can be further classified as an acute or chronic wound. An acute wound is one that does not have an underlying healing defect, and usually occurs secondarily to surgery or trauma in a healthy individual, healing quickly and completely. In contrast, a chronic wound is one that has a loss in tissue integrity, produced by insult or injury that is of extended duration or frequent recurrence. As used herein, the term "skin wound" refers to a break in the skin.

The term "open wound" is usually classified according to the object that caused the wound. This includes burns, incisions, lacerations, abrasions, puncture wounds, penetration wounds, gunshot wounds and the like. Incisions or incised wounds may be caused by a clean, sharp-edged object such as a knife, a razor, or a glass splinter. Incisions involving only the epidermis can be classified as cuts. Lacerations are irregular wounds caused by a blunt impact to soft tissue that lies over hard tissue (such as laceration of the skin covering the skull) or tearing of skin and other tissues (such as caused by childbirth). Lacerations may show bridging, as connective tissue or blood vessels are flattened against the underlying hard surface. Abrasions (grazes) are superficial wounds in which the topmost layer of the skin (the epidermis) is scraped off, and are often caused by a sliding fall onto a rough surface. Puncture wounds may be caused by an object puncturing the skin, such as a nail or needle. Penetration wounds may be caused by an object such as a knife entering the body. Gunshot wounds are caused by a bullet or similar projectile driving into or through the body. As such, there may be two wounds, one at the site of entry and one at the site of exit, which is generally known as a through-and-through.

The term "closed wound" refers to contusions, more commonly known as bruises, caused by blunt force trauma that damages tissue under the skin; hematomas, also called blood tumors, caused by damage to a blood vessel that in turn causes blood to collect under the skin; and crushing injuries, which may be caused by a great or extreme amount of force applied over a long period of time.

The term "scar" refers to an abnormal morphological structure resulting from a previous injury or wound (e.g., an incision, excision or trauma). Scars are composed of a connective tissue which is predominately a matrix of collagen types 1 and 3 and fibronectin. A scar may consist of collagen fibers in an abnormal organization (as seen in normal scars of the skin) or may be an abnormal accumulation of connective tissue (as seen in scars of the central nervous system or pathological scarring of the skin). The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion. Scar contractures are scars that cross joints or skin creases at right angles, and are prone to developing shortening or contracture. Scar contractures occur when the scar is not fully matured, often tend to be hypertrophic, and are typically disabling and dysfunctional.

A variety of conditions may cause scarring, including surgical wounds, burns, cuts, gunshot, etc. Scars commonly form as a result of facial plastic surgery, which includes, but is not limited to, rhytidectomy, blepharoplasty, rhinoplasty, otoplasty, mentoplasty, face lift, fore head lift, brow lift, facial scar revision, facial scar removal, laser surgery, skin resurfacing, wrinkle treatment, plasma skin regeneration, facial fat grafting, skin tightening, tattoo removal and hair replacement. Thus, this disclosure is advantageous to patients who undergo facial plastic surgery, particularly to aid with scarring and bruising, by speeding up wound healing and reducing scar formation. Scars also commonly form as a result of full-body plastic surgery, which includes, but is not limited to abdominoplasty, breast reduction, breast enhancement, body lift procedures, spider vein treatment, stretch mark treatment, liposuction, excess skin removal surgery, cellulite reduction treatment, body contouring, body resurfacing and body implants.

"Administering" refers to giving or applying to a subject a pharmaceutical remedy or formulation via a specific route, including but not limited to, topically, intradermal injection, intravenously, systemically, subcutaneously, intramuscularly, sublingually, and via inhalation or injection, irrigation or an osmotic pump.

Compositions, Devices and Methods

Described herein are compositions for promoting tissue reducing scarring during healing. The compositions include a porous scaffold and an effective dose of focal adhesion kinase (FAK) inhibitor. The FAK inhibitor is fabricated for controlled drug release and disposed in pores of the scaffold and the scaffold being configured to deliver to a delivery surface a dose of the FAK inhibitor effective to promote tissue healing at a controlled rate during a treatment time. The porous scaffold may include a hydrogel film, such as a pullulan-hydrogel film. The composition may be configured to deliver to the delivery surface a dose of the FAK inhibitor effective to reduce scarring of the tissue during the treatment time and/or to promote hair growth in the tissue during the treatment time. The composition may be configured as a wound dressing and may be flexible.

Provided herein are methods for promoting healing such as ameliorating the formation of scars and/or keloids and/or generating hair are provided, comprising the step of contacting a wound with an effective dose of an FAK inhibitor hydrogel as disclosed herein for a period of time sufficient to reduce scarring, form hair or form dermal appendages. Provided herein are methods for promoting tissue healing, including placing a composition comprising a porous scaffold and a focal adhesion kinase (FAK) inhibitor fabricated for controlled drug release disposed in pores of the scaffold; applying the composition to a tissue surface; and delivering from a delivery surface of the composition to the tissue a dose of the FAK inhibitor effective to promote tissue healing at a controlled rate during a treatment time. In some methods the composition includes a hydrogel, such as a pullulan-collagen hydrogel. In some methods the dose of the FAK inhibitor is effective to reduce scarring of the tissue during the treatment time. In some methods the FAK inhibitor is effective to reduce scarring of the tissue after the treatment time, e.g., through activation of healing pathways in the body. In some methods the dose of the FAK inhibitor is effective to promote hair growth in the tissue during (or after) the treatment time. For example, hair may continue to grow even after a porous scaffold is removed. In some methods the composition is configured as a wound dressing. In some methods FAK inhibitor is disposed on a delivery surface. In some methods the controlled rate comprises a rapid release rate (for release to a tissue surface) and a sustained release rate (for release to a tissue surface). In some methods FAKI for rapid release is released to the tissue surface within about 12 hours, about 24 hours or in between these times. In some methods the FAKI for sustained release is released to the delivery surface over a period of up to about 24 hours, 48 hours, 72 hours or 96 hours or any length of time in between. In some methods the FAKI for sustained release is released to the tissue surface over a period of up to about 24 hours, 48 hours, 72 hours or 96 hours or any length of time in between. Some methods include removing the composition from the tissue surface such as by lifting or pulling it from the surface. Some methods include biodegrading the composition. Some methods include repeating the placing and delivering steps at least 2 times, at least 3 times, at least 10 times, at least 20 times or at least 30 times (e.g., with a fresh composition). In some methods FAK inhibitor is VS-6062 (PF-562271), or a benzenesulfonate salt of PF-562271. In some methods wherein about 30% of the total FAKI present in the composition to about 75% of the total FAKI present in the composition is delivered.

The hydrogel may be maintained in contact with the wound (tissue surface) for a period of time, e.g. for at least about 1 day, at least about 2 days, at least about 3 days, at least about 1 week, at least about 10 days, at least about 2 weeks, at least about 3 weeks, or more. For example, in some variations, it is desirable to apply the hydrogel to the wound site from about one to about three days following injury, i.e., during an initial period such as the early part of the proliferative phase. Hydrogels may be applied to a fresh wound caused by a scar removal procedure. In some instances, the hydrogel will be applied up to seven days following injury, i.e., later in the proliferative phase. For example, swelling and wound exudates may indicate that the hydrogel be applied later than three days following injury. In some applications, a first hydrogel can be applied within an initial period following injury, e.g., within the first three days, and then removed, and a second hydrogel can be applied thereafter. The second hydrogel can be adapted to changes in the skin and tissue surrounding the wound that can occur after the initial period, e.g., decreased swelling and exudates.

Described herein is a method of manufacturing a composition with a porous scaffold for treating a wound including forming a mixture comprising a focal adhesion kinase (FAK) inhibitor, pullulan, collagen, and a porogen; and removing the porogen and/or dehydrating the mixture to thereby create a composition with a porous scaffold having focal adhesion kinase (FAK) inhibitor disposed in pores of the scaffold fabricated for controlled drug release. In some embodiments, the porous scaffold includes a hydrogel, e.g., a pullulan and collagen hydrogel. Some methods include placing FAK inhibitor on a surface of the composition. Some such methods further include cross-linking the pullulan with sodium trimetaphosphate (STMP) and/or sodium tripolyphosphate (STPP) or another cross-linker.

Some methods include crystalizing the porogen prior to the removing step. For example, a salt porogen such as a potassium or sodium or another salt as described elsewhere herein may be used. In some methods composition includes a non-uniform distribution of FAK inhibitor. For example, the FAK inhibitor may be concentrated along pores. The FAK inhibitor may also or instead be concentrated along a particular layer in a multi-layer structure or at an outside surface of the composition (e.g., at the outside surface of a device).

The subject methods find use in any application in which the treatment of a wound of a subject is desired. Generally, such subjects are "mammals" or "mammalian", where these terms are used broadly to describe organisms which are within the class mammalia, including the order carnivore (e.g., dogs and cats), rodentia (e.g., mice, guinea pigs, and rats), and primates (e.g., humans, chimpanzees, and monkeys). In many embodiments, the subject is a human.

Accordingly, the subject methods may be used to treat a wide variety of open- and closed-skin wounds such that the subject methods may be used to treat wounds that have resulted from a variety of causes, e.g., as a result of a condition such as a disease state, a physical injury such as a fall, scrape, stab wound, gun shot, surgical wound, infection, etc., wartime injuries such as bombs, bullets, shrapnel. Likewise, the subject methods may treat wounds of various dimensions. For example, the subject methods may be employed to with both deep tissue wounds and shallow or superficial wounds, where certain wounds may have depths that reach the muscle. Wounds may be confined to the epidermis such that they do not penetrate into the dermal layer, may be as deep as the dermis or deeper, e.g., may penetrate to or through the dermis and even to or through the subcutaneous tissue layer or deeper, e.g., may penetrate through or to the muscle layer or further. For example, the subject methods may be used to debride wounds that having a depth that ranges from about 0.005 mm to about 2.35 mm, e.g., from about 0.007 mm to about 2.3 mm, e.g., from about 0.01 mm to about 2 mm.

A wound dressing may comprise an effective dose of an FAK inhibitor imprinted or surface-applied to a pullulan/collagen hydrogel, which hydrogel may be attached or adhered to a substrate, e.g. a breathable protective layer, or other protective film. Alternatively the dressing may be separately configured from a protective dressing. The support is generally made of a flexible material which is capable of fitting in the movement of the human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like. By "flexible" it is meant that the support may be substantially bent or folded without breaking, tearing, ripping, etc. The support may be porous or non-porous, but is typically non-porous or impermeable to the hydrogel composition, active agent if employed and fluids, e.g., any fluids exuded from the wound site.

The length and width dimensions of the support are typically substantially commensurate, including exactly commensurate, with the length and width dimensions of the patch composition with which it is associated. The support layer typically may have a thickness that ranges from about 10 µm to about 1000 µm, but may be less than about 10 µm and/or greater than 1000 µm in certain embodiments.

In addition to the hydrogel and the optional support layer, the dressing may also include a release film on the surface of the hydrogel composition layer opposite a backing that provides for protection of the patch layer from the environment. The release film may be any convenient material, where representative release films include polyesters, such as PET or PP, and the like.

The shape of the dressing may vary, where representative shapes include square, rectangle, oval, circle, triangular, etc. The size of the dressing may also vary, where in many embodiments the size of the hydrogel ranges from about 1 cm2 or less to about 1000 cm2 or more, e.g., in certain embodiments ranges from about 10 to about 300 $cm^2$, e.g., from about 20 to about 200 $cm^2$, e.g., about 130 $cm^2$ to about 150 $cm^2$. In certain embodiments, the surface area is sufficient to cover a substantial portion or even the entire truck or even a substantial portion of the entire body or even the entire body of a subject. Accordingly, the surface area may range from about 1000 $cm^2$ to about 5000 $cm^2$ or more. It should be noted that the above manufacturing protocol is merely representative. Any convenient protocol that is capable of producing the subject hydrogel patch compositions, as described above, may be employed.

The devices and bandages described herein may have any suitable shape. For example, the devices or bandages may be rectangular, square, circular, oval, toroidal, or segments or combinations thereof. In many variations, the devices will be flexible and planar to allow conformal placement against skin. Of course, the devices and bandages may also be of any suitable size, to deal with a variety of wounds. In some variations, the devices and bandages may be cut immediately prior to use from a roll or sheet of bandage to ensure appropriate coverage of the wound site. Devices and bandages can extend out to about 20 cm (about 8 inches) from the wound in some instances, and in other instances the devices or bandages can extend about 2, 4, 6, 8, 10, 12, 14, 16, or 18 cm from the wound, where "about" qualifies each of the distances. In still other variations, the bandages can extend about 22 cm, about 24 cm, about 26 cm, or even more, from the wound. In some variations, the devices are made from a polymer, for example, a shape memory polymer. Any suitable shape memory polymer may be used, e.g., styrene-based, epoxy-based, or acrylate-based shape memory polymers.

Kits for ameliorating the formation of scars and/or keloids and/or developing hair and skin appendages are also described here. In general, the kits comprise in packaged combination a unit dosage of an effective amount of an FAKI containing hydrogel as described herein. Multiple doses in a kit may be designed to be applied in parallel. For example, some kits may include one hydrogel to be applied during an initial period such as the early part of the proliferative phase of wound healing, e.g., up to three days after injury, and then removed and a second hydrogel to be applied thereafter. Some kits may contain at least one wound dressing, or at least one wound cleanser, or other components desirable or suitable for wound healing applications. The kits may also comprise instructions for using the devices and/or other components contained therein.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention.

Experimental

Controlled Delivery of a Focal Adhesion Kinase Inhibitor Results in Accelerated Wound Closure with Decreased Scar Formation Formation of scars following wounding or trauma represents a significant healthcare burden costing the economy billions of dollars every year. Activation of focal adhesion kinase (FAK) has been shown to play a pivotal role in transducing mechanical signals to elicit fibrotic responses and scar formation during wound repair. We have previously shown that inhibition of FAK using local injections of a small molecule FAK inhibitor (FAKI) can attenuate scar development in a hypertrophic scar model. Clinical translation of FAKI therapy has been challenging, however, due to the lack of an effective drug delivery system for extensive burn injuries, blast injuries, and large excisional injuries. To address this issue, we have developed a pullulan collagen-based hydrogel to deliver FAKI to excisional and burn wounds in mice. Specifically, two distinct drug laden hydrogels were developed for rapid or sustained release of FAKI for treatment of burn wounds and excisional wounds, respectively. Controlled delivery of FAKI via pullulan collagen hydrogels accelerated wound healing, reduced collagen deposition and activation of scar forming myofibroblasts in both wound healing models. Our study highlights a biomaterial-based drug delivery approach for wound and scar management that has significant translational implications.

A pullulan-collagen based hydrogel system is used for delivery of FAKI to healing wounds. Efficacy of FAKI hydrogel therapy was evaluated in large and deep murine excisional and burn wound models. Two distinct types of hydrogels were developed: i.) sustained-release hydrogels and ii.) rapid-release hydrogels. To develop sustained-release hydrogels, we employed a molecular imprinting technique to incorporate FAKI into the porous hydrogel, which enabled slow and sustained release of FAKI to the wound environment over a few days. These hydrogels were used for controlled delivery of FAKI to splinted excisional wounds in mice. Burn wounds, however, are associated with increased serous drainage and more frequent dressing changes are required. To accommodate this, we employed FAKI surface incorporation method that allows for rapid release of FAKI within a few hours.

Here, we report that FAKI significantly improved wound healing of murine wounds and attenuated fibrogenic activities following wound healing. Our study highlights a biomaterial-based anti-scar drug delivery approach for wound and scar management.

Figure 1:
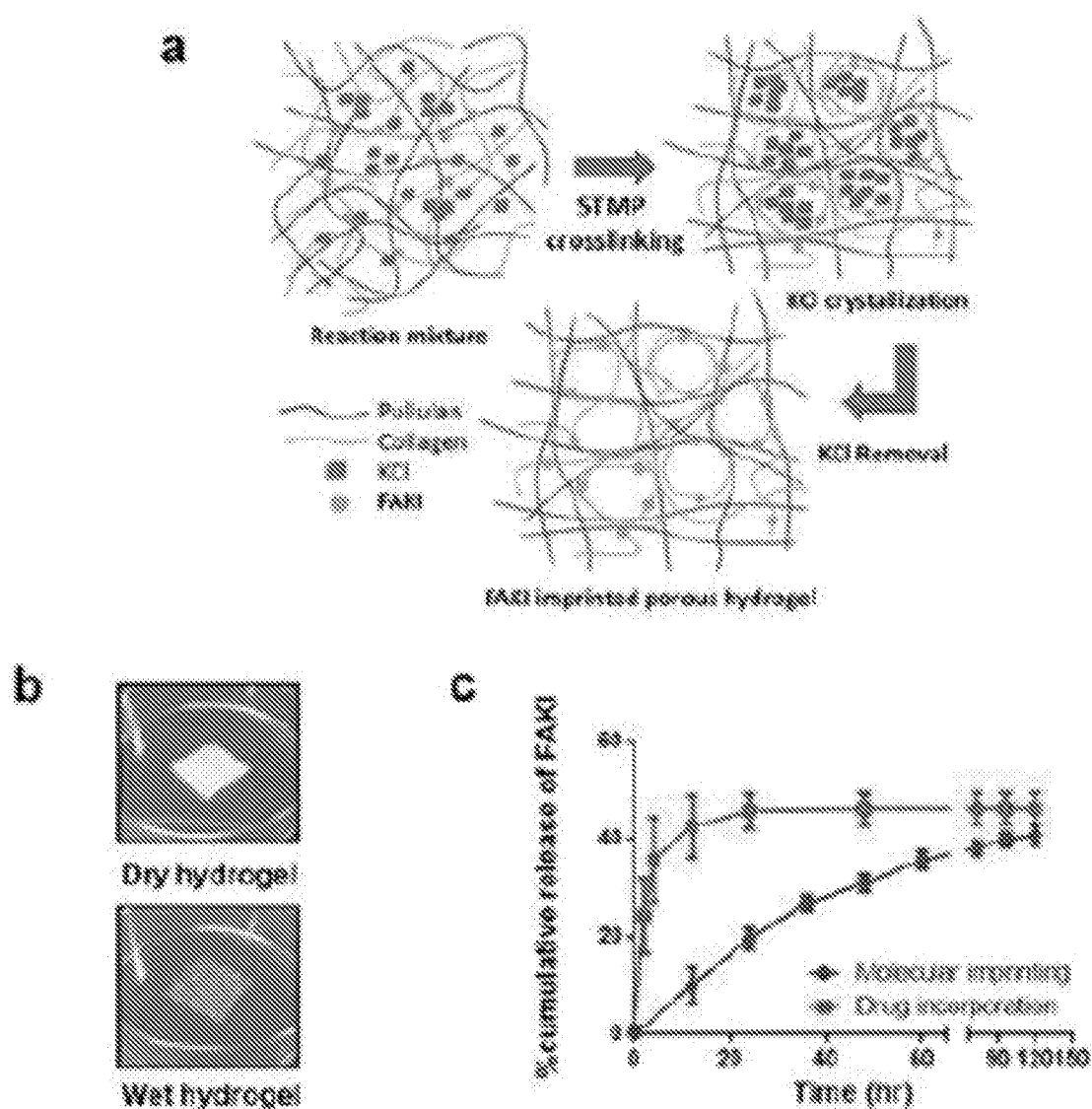
FIG. 1A-FIG. 1C show construction of FAK inhibitor ("FAKI")-releasing pullulan-collagen hydrogels and in vitro release profiles.

In vitro drug release profiles for FAKI from pullulan-collagen hydrogels. We have previously reported fabrication methods and characterization of a soft, dermal-like pullulan-collagen hydrogel matrix with the capacity of cell or small molecule drug incorporation. (Wong et al., 2011c and FIG. 1A). Hydrogel swelling and in vitro degradation behavior did not change with FAKI loading (swelling ratio with FAKI 32.15±0.56 vs. without FAKI 30.87±0.84) (FIG. 1B). Mass spectrometry confirmed that FAKI structural integrity was maintained after incorporation into hydrogels.

Figure 6:
Figure 6:
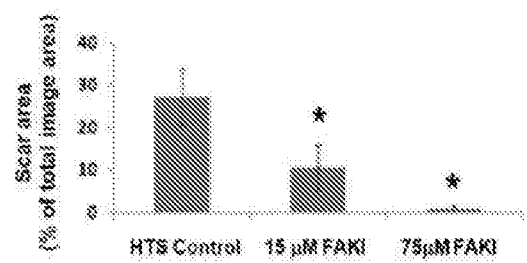

Two distinct drug release kinetics were adopted for effective delivery of FAKI depending on the type of injury. Molecular imprinting technique produced sustained-release kinetics, exhibiting optimal local concentrations of FAKI during the first few days following wounding (FIG. 1C). Using our previously reported murine HTS model (Aarabi et al., 2007; Wong et al, 2011a), this FAKI concentration was effective in reducing scar formation when locally injected at the wound site daily for 10 consecutive days (FIG. 6). Sustained-release FAKI hydrogels were used for splinted excisional wounds. Since burn wounds produce abundant serous drainage after debridement that soil dressings, frequent change of hydrogel and bandages was necessary for prevention of any infection and a rapid release profile is desirable. To standardize the dose of FAKI applied to both wound types, we adopted a hydrogel scaffold prepared by surface drug incorporation method that rapidly releases FAKI.

Hydrogels produced with molecular imprinting steadily released FAKI over several days with near complete release of FAKI occurring approximately at Day 4. The surface incorporation method was complete within 24 hours. Both type of hydrogels released about 40-45% of the total amount initially incorporated (FIG. 1C). For rapidly released FAKI, total amount of drug released within 24 hrs. did not exceed its skin toxicity levels (FIG. 6). In in vitro experiments, degradation of hydrogels was not visually observable. Because hydrogel and dressings are changed frequently when used in vivo, our in vitro release study up to the first 72 hrs. is biologically relevant.

Figure 2A:
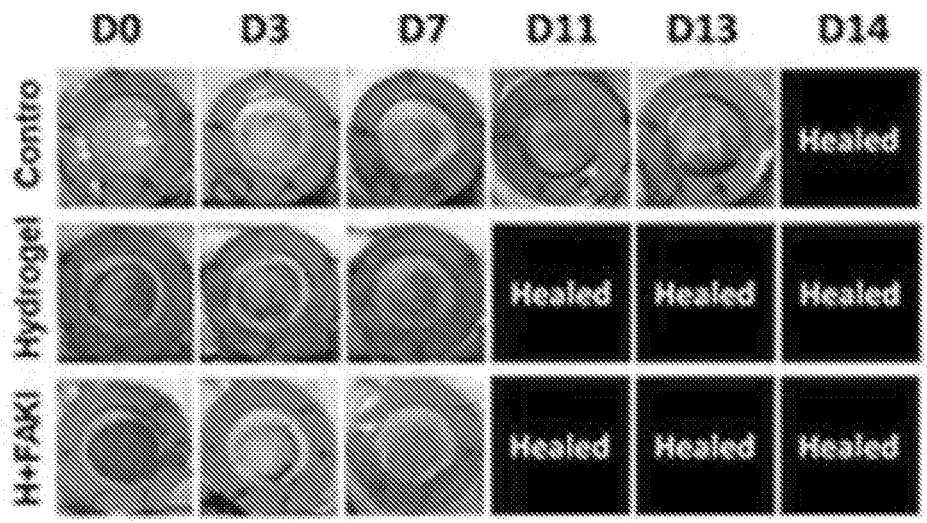
FIG. 2A-FIG. 2C shows FAKI delivered via hydrogel accelerated wound healing in a splinted full-thickness excisional wound model.
Figure 2B:
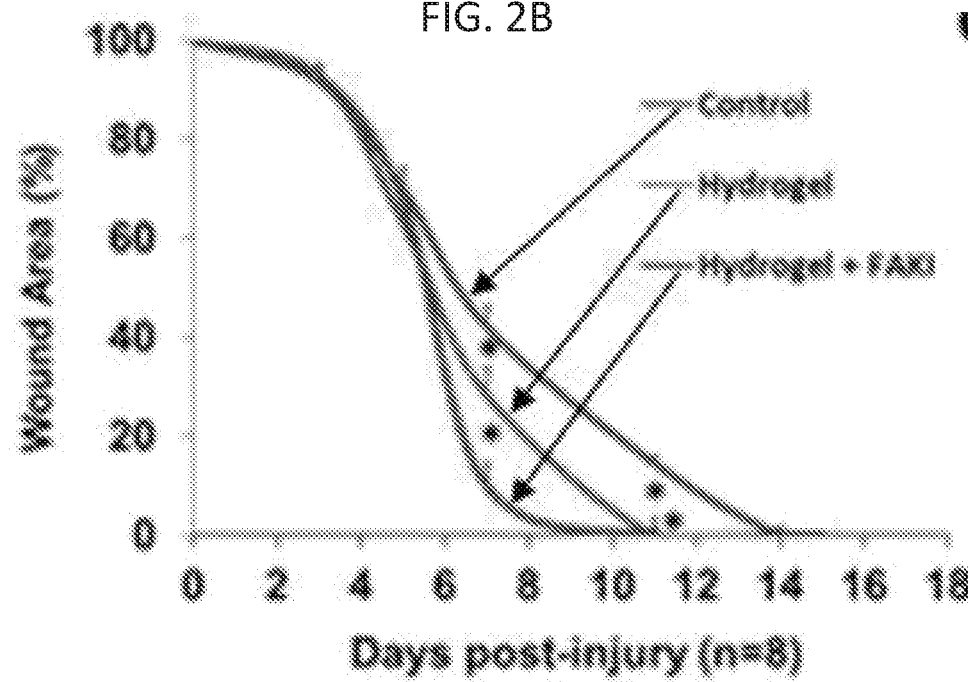
Figure 2C:
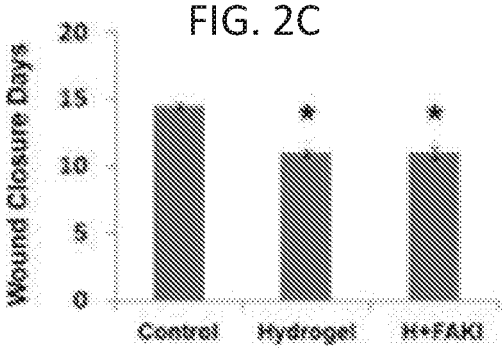

FAKI delivered via hydrogel enhances healing of excisional wounds. Splinted wounds in mice, which replicate the mechanism of wound healing via re-epithelialization as seen in humans (Wong et al., 2011b) were treated with sustained-release FAKI-laden hydrogels daily until the wounds completely closed. From Day 0 (when the wounds were created), excisional wounds received FAKI hydrogels that release FAKI in a sustained fashion. Used hydrogels were removed and replaced with fresh hydrogels and adhesive bandages every other day. Excisional wounds treated with FAKI healed significantly earlier than those without treatment, and complete closure occurred on Day 11 vs. Day 14 post-injury for control wounds ($P<0.05$; FIG. 2). Blank hydrogel also accelerated wound closure, suggesting that the scaffold alone can produce beneficial wound healing environment for excisional wounds, consistent with previous reports (Wong et al., 2011c; Wong et al., 2011d). Bulk degradation of hydrogels, assessed by visual inspection, did not occur within the time-course tested, therefore, we speculate that there was no massive FAKI release accompanied by in vivo scaffold degradation. All animals tolerated localized FAKI therapy and all wounds did not show signs of infection.

FAKI delivered via hydrogel suppresses scar-forming pro-fibrotic activity in excisional wounds. Without scar-promoting stimuli (e.g., mechanical strain), murine skin typically does not develop elevated HTS; however, pro-fibrotic events following injury can be measured by the amount of collagen deposition and the presence of myofibroblasts after the wounds are healed. On Day 17 post-injury, histological analyses of collagen staining demonstrated that collagen deposition was greatest in the control wounds, and least amount of collagen was observed in the wounds treated with FAKI. Protein expression of α-SMA, a marker of myofibroblast differentiation and fibrogenesis, was significantly decreased with FAKI treatment. These results were consistent with the decreased level of phosphorylation of FAK (p-FAK) in wound tissue lysates collected on Day 10 post-injury (FIGS. 3E and F).

Of interest, p-FAK inhibition was not detected when FAKI dissolved in 10% DMSO was dripped on to the wound site daily for 10 days, demonstrating that FAKI-imprinted hydrogel scaffold allowed sustained and controlled delivery of FAKI to the local site for improved activity. Activation of Akt (p-Akt) and FAKI-mediated inhibition of Akt phosphorylation was also examined in tissues harvested on Day 17. Activation of Akt was prominent in the epidermal layer during this remodeling phase and topically delivered FAKI substantially inhibited Akt activation (FIGS. 3G and H).

Mechanical properties of healed excisional wounds are improved with FAKI treatment. Cutaneous scars formed following wound healing are often associated with altered structural integrity and weak skin mechanical properties. We tested whether FAKI treatment could improve mechanical profile of healed wounds. Young's modulus of healed skin was significantly higher in hydrogel alone and FAKI hydrogel-treated wounds, compared with the control (FIG. 4) demonstrating that the mechanical integrity of healed skin is improved and therefore the ability to resist external mechanical stress is enhanced. Young's modulus was highest with FAKI treatment. We also examined the ultimate tensile strength (UTS) that measures the maximum stress that the skin can withstand when stretched and FAKI-treated skin showed the greatest UTS. Collectively, FAKI is beneficial towards improving the physical integrity of healed skin presumably via modulation of collagen deposition and the extracellular matrix composition of the dermis during wound healing and remodeling processes.

FAKI delivered via hydrogel enhances healing of contact burn wounds. Prolonged healing associated with severe deep dermal burn injuries can commonly lead to HTS formation. We used a murine full-thickness contact burn wound model to study the anti-fibrotic effects of FAKI, and whether FAKI can accelerate healing of burn wounds. After debridement at 72 hrs post injury, burn wounds were treated with hydrogels that rapidly release FAKI. Unlike excisional wounds, burn wounds showed increased drainage from the wound site and adjacent tissues until the wounds re-epithelialized. As a result, more frequent dressing changes were necessary. For the first 3 days following initial treatment, hydrogels and bandages were replaced every day and then every other day thereafter. Compared to hydrogel alone or control wounds, burn wounds treated with FAKI showed accelerated wound closure without complications (FIG. 5). Similar to our observations with excisional wounds, bulk degradation of hydrogels did not occur. After complete closure, α-SMA expression in the wound lesions were measured, which was significantly decreased with FAKI treatment (FIG. 5).

Topical Delivery of a Focal Adhesion Kinase Inhibitor Results in Accelerated Healing, Decreased Scar Formation, and Restores Hair Follicles and Skin Appendages Here, we report that FAKI in a pullulan-collagen device significantly accelerated wound healing, decreased scar formation, and restored hair follicles and skin appendages in a large animal model shown to be most similar to human skin.

Red Duroc pigs can develop thick, long-lived human-like scars upon deep dermal wounding. Sustained-release FAKI hydrogels (shown in FIG. 1A-1C and described elsewhere herein) were used on deep dermal wounds in Red Duroc pigs. FIG. 7A-FIG. 7D shows the setup for analyzing the effects of topical treatment of FAKI applied in a hydrogel device to deep cutaneous wounds in a red Duroc pig model. FIG. 7A shows the region along the back of the pig used for testing. FIG. 7B shows a porcine deep wound with the removed skin. FIG. 7C shows a cross sectional view of intact pig skin. FIG. 7D shows a cross-sectional view of wound pig skin with a wounded depth of 0.06 inches (in). FIG. 7E shows the timeline from the day of injury (D0) to 180 postoperative days (D180). FAKI in a pullulan-collagen device was placed over the wound and for the first 21 days, was replaced every other day. From 22 to 90, the FAKI pullulan-collagen device was changed 2×/week. From postoperative day 91 to postoperative day 180, the wound was left to heal without any pullulan-collagen device applied. Biopsy samples, photographs, and tissue harvest were taken as indicated.

FAKI delivered via hydrogel significantly accelerates wound healing of deep cutaneous wounds. FIG. 8A-FIG. 8C show that topically treating deep cutaneous wounds in Duroc pigs with FAKI hydrogel accelerates wound healing. N=8 wounds tested for each condition. Initial wound size=25 cm$^2$. FIG. 8A shows photographs of the wounds taken from postoperative day (POD) 2 to POD 30 as described above and in FIGS. 7A-7E. Wounds treated with FAKI hydrogel are visibly more healed at POD 11, POD 21, and POD 30, compared with untreated wounds or wounds treated with hydrogel alone. In addition to visibly improved appearance, wounds treated with FAKI hydrogel were significantly smaller. The wound area remaining of wounds treated with FAKI delivered via hydrogel were compared with untreated control wounds and wounds treated with hydrogel only. Wound size was measured and graphed as a % of the original wound area and results are shown in FIG. 8B. FAKI hydrogel treated wounds were smaller after POD 4 compared with controls and by POD 14, just about all of the FAKI hydrogel treated wounds had closed, while about 20% of untreated (control) wounds had not closed and remained open, a statistically significant difference (*). By POD 17, all of the FAKI hydrogel treated wounds had closed while about 10% of untreated (control) wounds were still open, a statistically significant difference (*). Hydrogel alone accelerated wound healing, suggesting that the scaffold alone can produce beneficial wound healing environment for excisional wounds, as indicated above. FIG. 8C shows that untreated wounds or wounds treated with hydrogel alone take 25 days to fully close, while wounds treated with FAKI in a hydrogel device are closed by POD 14, a statistically significant result (Δ).

FAKI delivered via hydrogel significantly improves scar appearance FIG. 9A-FIG. 9B and FIG. 10A-FIG. 10B show that topically treating deep cutaneous wounds with FAKI delivered via hydrogel significantly improves scar appearance at POD 45, POD 60, POD 90 (3 months), and POD 180 (6 months). FIG. 9B shows results from Visual Analog Scale (VAS) analysis of scars. Visual Analog Scale scores were assessed by four blinded scar experts for untreated control, hydrogel treated and FAKI via hydrogel treatment. The scarring in the control was arbitrarily set at 100 and results were scaled relative to the control. Wounds treated with FAKI via hydrogel showed significantly less scarring and better visual appearance compared with untreated control, about 58 on a scale of 100 (FIG. 9B; ΔP<0.001). Hydrogel treatment alone yielded a slight improvement relative to the untreated control. The trend persists at POD 180 (FIG. 10B; ΔP<0.001).

FAKI delivered via hydrogel leads to noticeable hair formation and restoration of hair follicles and skin appendages. Surprisingly, deep cutaneous wounds topically treated with FAKI delivered via hydrogel show noticeable hair growth that is absent from control treatment or wounds treated with hydrogel alone, as shown in FIG. 10B. FIG. 11A-FIG. 11C show results from POD 90. Images in FIG. 11A show Trichrome staining at POD 90. Arrow 1 points to a hair follicle. Arrow 3 points to a hair follicle with surrounding glandular structures. Arrow 2 and Arrows 4-6 point to cutaneous glands (sweat and sebaceous glands). Wounds treated with FAKI delivered via hydrogel have significantly more hair follicles at POD 90 (an average of about 2.8 vs 0.6 in the control; #P<0.01 Control vs H+FAKI) and this difference persists at POD 180. Wounds treated with FAKI delivered via hydrogel have a significantly larger number of glands (sebaceous and sweat) at POD 90 (about 7 in the hydrogel+FAKI treated wound vs 0.1 in the control; *P 0.001 Control vs H+FAKI) and this difference persists at POD 180 (about vs X in the control).

FAKI delivered via hydrogel suppresses scar-forming pro-fibrotic activity in excisional wounds Similar to as shown above for excisional wounds in mice, FIG. 12A shows that FAKI delivered via hydrogel significantly decreases α-smooth muscle action (α-SMA) expression in wounds treated with FAKI delivered via hydrogel vs untreated controls at POD 60 and POD 90. FIG. 12B (POD 60) shows that level of α-SMA expression is significantly lower in treated wounds (about 2% of the areas is stained green (indicative of α-SMA) in the treated sample vs. about 28% in the untreated control; *p, 0.001) and this trend persists at POD 90 (FIG. 12C). α-smooth muscle action (α-SMA) was quantified by blinded observers for randomly selected regions within scar lesions.

FAKI delivered via hydrogel results in dermal collagen structure that resembles unwounded skin FIG. 13A-FIG. 13C show that wounds treated with FAKI delivered via hydrogel results in dermal collagen structure that resembles unwounded skin. FIG. 13A shows that tissue from pigs treated topically with FAKI delivered via hydrogel has shorter fibrils compared with either untreated control wounds or hydrogel treated wounds (compare the third row panel with the top and second row panels in FIG. 13A). Rather, the collagen fibrils from the tissue from pigs treated topically with FAKI far more closely resembles tissue from an unwounded animal (bottom panel). FIG. 13B shows results from quantitating collagen fibril length from samples stained such as those shown in FIG. 13A. Wounds treated topically with FAKI delivered via hydrogel showed significantly shorter fibrils compared with untreated control wounds (p<0.01). FIG. 13C shows the number of collagen fibrils from panels stained such as shown in FIG. 13A. Wounds treated topically with FAKI delivered via hydrogel showed significantly more fibrils compared with untreated control wounds (p<0.05). The horizontal line in the middle of the bar graph represent the median and the X represents the mean. N=9 images for control, hydrogel and hydrogel+FAKI). N=4 images for unwounded.

FIG. 15A-FIG. 15B shows safety of FAKI delivered locally via hydrogel. FIG. 15A shows FIG. 15A-FIG. 15B shows toxicology and pharmacokinetic studies of FAKI delivered locally via hydrogel. The systemic absorption of FAKI molecule was examined from serum at various time points after application and FIG. 15A shows the results.

Systemic absorption of locally delivered FAKI to 5-7% of the total body surface was insignificant (1 ng/ml=2 nM FAKI). FAKI hydrogel samples were applied daily at high concentrations of FAKI (150 um FAKI, 1.5 mM FAKI) to unwounded skin and the results are shown in FIG. 15B. Daily application of FAKI, even at high concentrations, did not result in irritation or sensitization of skin.

At present, clinically available therapies to limit abnormal healing and scarring associated with burns and traumatic wounds are minimally effective with weak scientific rationale. The integrin/FAK mechanotransduction signaling pathway plays a central role in cutaneous scar formation following injury, by mediating mechanical stress signals to promote fibrogenic processes through inflammatory mediators. Thus, suppression of FAK signal transducers is a promising strategy for scarless wound healing in large and deep dermal wounds. Newer generation small molecule inhibitors of FAK, including VS-6062 and improved VS-6063/defactinib, have proven effective in the treatment of advanced solid tumors in clinical trials. VS-6062 displayed desired pharmacokinetics in these trials but was discontinued as an anti-cancer agent due to potential drug-drug interactions when dosed orally. With oral administration, major systemic toxicities were observed with nausea/vomiting and gastrointestinal-related adverse effects in these trials. Localized topical delivery of this compound circumvents systemic absorption and subsequent toxicities and was used in our studies.

In previous murine studies, intradermal injection of a small molecule FAK inhibitor (PF573228) suppressed inflammatory chemokine pathways and attenuated scarring in vivo in the incisional HTS model. Large areas of deep dermal wounds, however, are difficult to treat by dermal injection, and targeted topical delivery of pharmacological agents is more likely to be the favored modality in the clinics. Biomaterial-based approaches for wound treatment have been studied extensively in the past. Various chitosan or hyaluronan hydrogel composites have been tested on dermal wounds with beneficial effects on cutaneous healing and regeneration.

Previously, our group reported that biodegradable pullulan-collagen dermal hydrogel alone can augment early wound healing in murine wounds. Pullulan hydrogels are non-toxic and modifiable and exhibit ideal water retention capabilities. The porous matrix also has multiple functional groups allowing crosslinking and the potential to serve as a structured template for cell-based and/or biomolecule delivery for various cutaneous healing disorders. Using this bioengineered matrix, we delivered mesenchymal stem cells to high oxidative-stress wounds for restoration of skin cell populations.

The present findings are the first to deliver an anti-scarring agent in a pullulan-collagen hydrogel for open wounds. Molecular imprinting techniques to encapsulate FAKI combined with unique hydrogel fabrication methods allowed precisely controlled sustained release of FAKI from the hydrogel scaffold for sustained release, rapid release, or a combination of the two. As shown herein, FAKI therapy significantly accelerated the healing of full-thickness excisional and burn wounds and reduced scar formation. Acceleration of wound healing is likely due to the inhibitory effects of FAKI on early immune cell responses (e.g., proliferation and migration) and inflammation.

Figure 3:
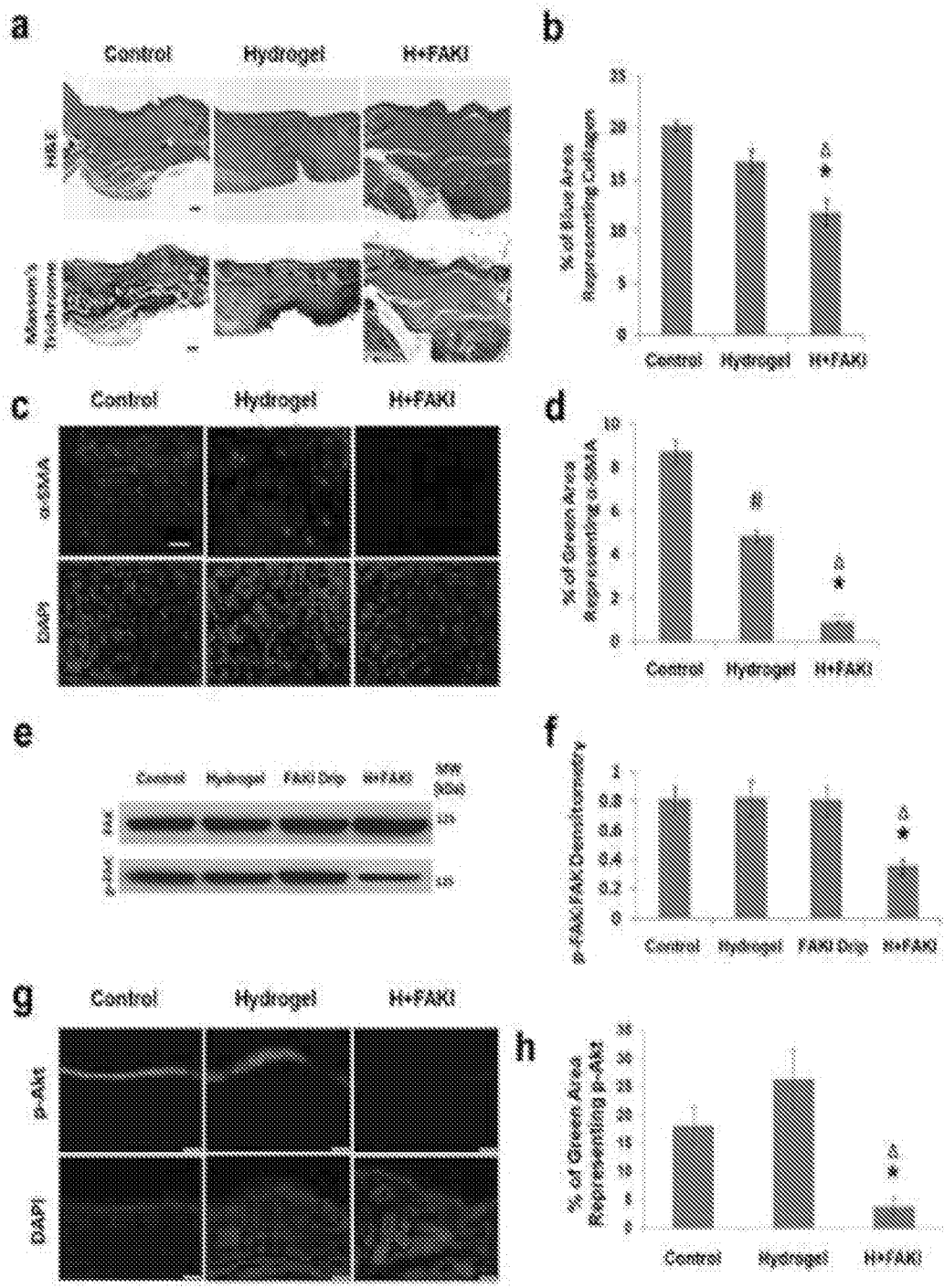
FIG. 3A-FIG. 3H show decreased pro-fibrotic activity with FAKI treatment in a splinted full-thickness excisional wound model.

The present studies provide mechanistic insight into FAK-mediated mechanotransduction and anti-fibrosis therapeutics. We demonstrate that FAKI inhibits activation of AKT, suggesting that FAK may act through multiple downstream effector proteins in the healing skin to augment fibrotic processes (FIG. 3). Although pullulan-collagen hydrogel alone was shown to be beneficial in promoting healing, it had little or no effect on burn wounds.

Figure 4:
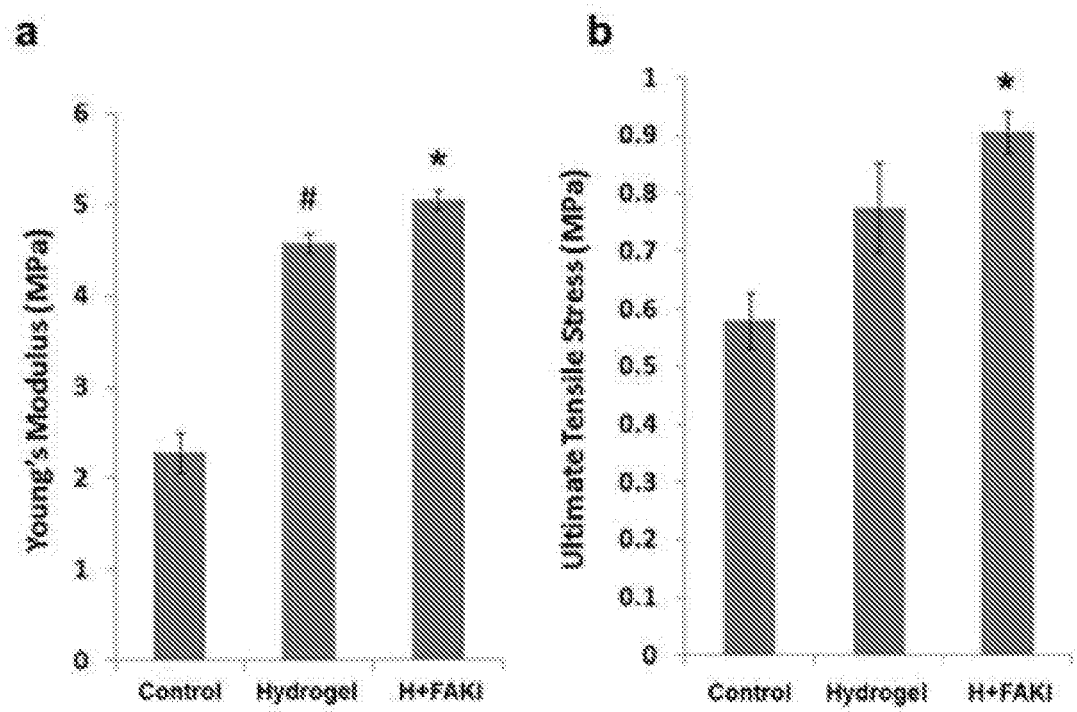
FIG. 4A-FIG. 4B show enhanced mechanical properties with FAKI treatment. Young's Modulus (MPa) (FIG. 4A)
Figure 5A:
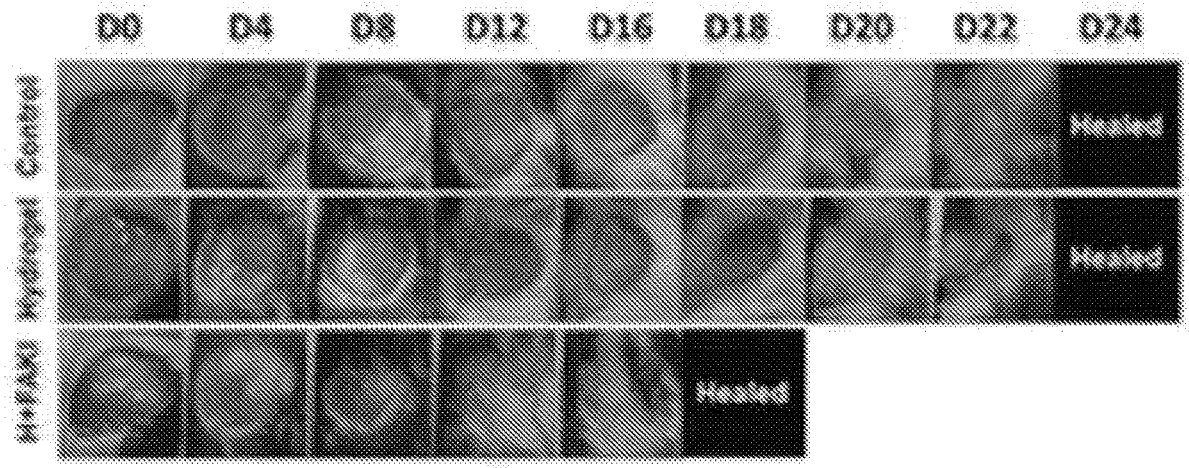
Figure 5B:
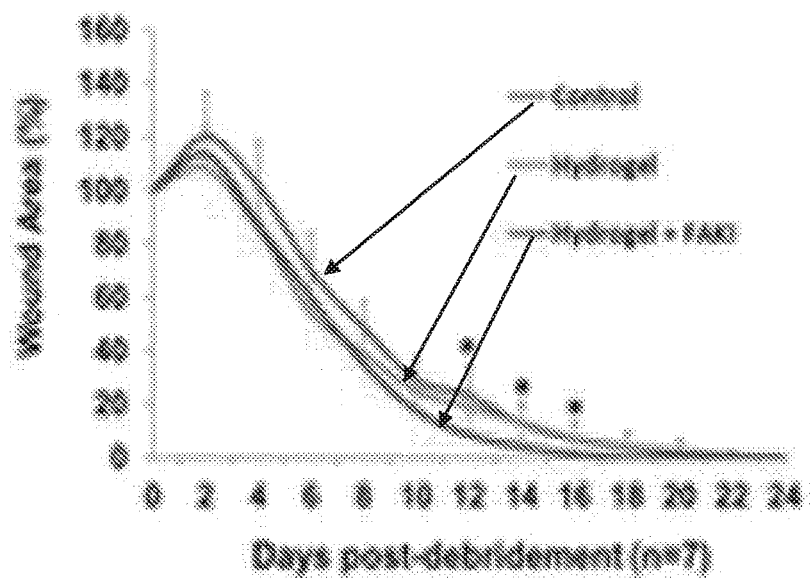
Figure 5C:
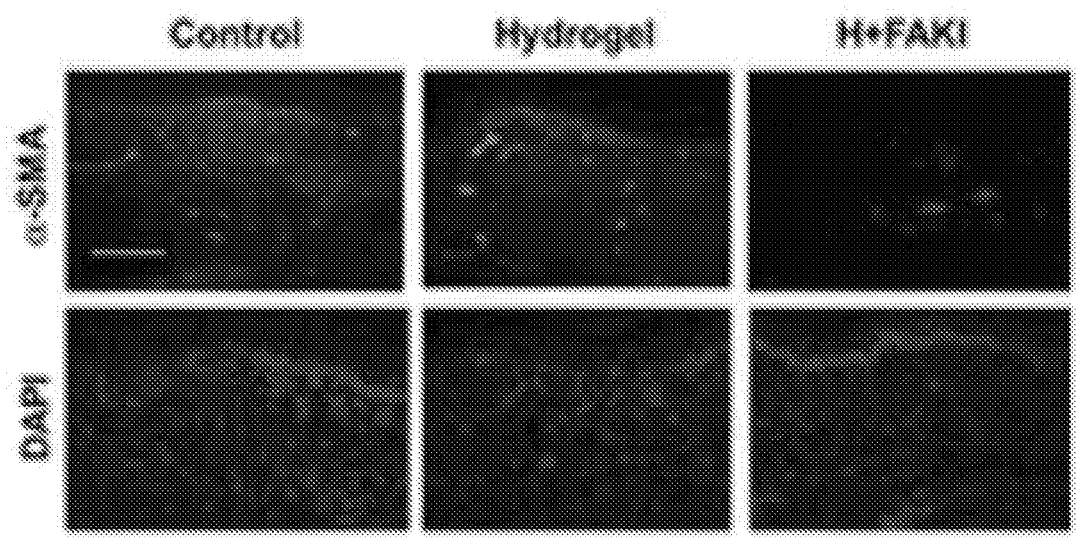
Figure 5D:
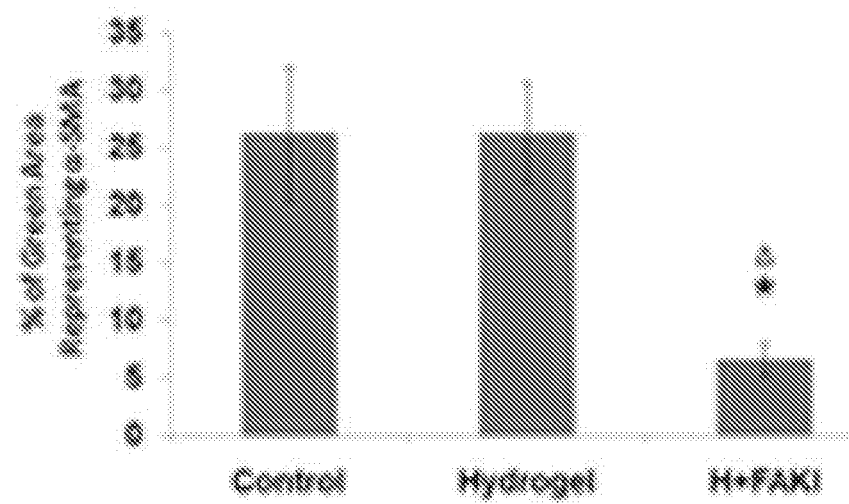

Since burn injuries are pathologically distinct from surgically excised wounds and often induce metabolic and inflammatory changes, we postulate that these differential effects could originate from different physiological responses to different types of injury. Further, the mechanical integrity of reconstituted skin after FAKI treatment is also improved. We have employed direct examination of mechanical integrity using tensile testing and calculated the Young's modulus and ultimate tensile strength (FIG. 4). FAKI-treated skin displayed the greatest Young's modulus as well as ultimate tensile strength, both measures of physical integrity of healed skin. Thus, the ability of healed skin to withstand deformation and breakdown in response to external forces or stress is enhanced with FAKI treatment relative to the hydrogel alone.

In conclusion, FAKI therapy via pullulan-collagen hydrogel scaffold was shown to be effective in reducing scar formation while promoting healing of excisional and burn wounds in mouse models. Our biomaterial-based delivery of FAKI holds great potential as an effective therapeutic strategy for scar management of large and deep dermal wounds. Results of this study enable the translation of FAKI scar reduction therapy in a highly translational preclinical large animal model for use in human clinical trials.

Materials and Methods

Construction of biocompatible FAKI-releasing hydrogel scaffold. FAKI, VS-6062 (previously PF-562271), was provided by Verastem, Inc. (Needham, MA). Porous pullulan collagen hydrogels were fabricated as previously described (Wong et al., 2011c). Hydrogel constructs containing FAKI were prepared either by molecular imprinting (sustained release) or surface incorporation (rapid release). Briefly, 1 g of pullulan (TCI, Tokyo, Japan) was mixed with 1 g of trisodium trimetaphosphate (STMP) (Sigma-Aldrich, St. Louis, MO) and 1 g of potassium chloride (Fisher Scientific, Hampton, NH). Collagen solution (Corning, Corning, NY) containing 50 mg of rat tail collagen I, 5% (w/w) of the weight of pullulan, was added to the mixture. For molecular imprinting (FIG. 1A), 10 mg of VS-6062 (FAKI) in 1 ml of 5% dimethyl sulfoxide (DMSO) was added to the mixture. Sodium hydroxide (0.65 ml of 1N solution) was then added followed by deionized water to a total of 10 ml. The mixture was gently vortexed for 15 min for homogenous distribution. When the viscosity of the mixture increased due to cross-linking of pullulan, the mixture was poured onto a Teflon sheet and compressed to create 2 mm-thick films. Films were allowed to dry and were washed with water until the pH of the wash solution was 7.0. Approximately 50% of FAKI was present in the hydrogel after this wash step. Swollen hydrogels were frozen at −80° C., and then lyophilized. For surface incorporation method, a blank hydrogel was made first, and then 5 mg of FAKI dissolved in ethanol was spread uniformly onto the dried hydrogels followed by evaporation of the solvent. Finally, hydrogel films were stored in a moisture-free container at 4° C. until used.

Water absorption/Swelling properties: Hydrogels constructed with and without FAKI were tested for their swelling behavior in PBS. Lyophilized hydrogels containing 5% collagen with and without FAKI were cut into a circular patch using a 0.8 mm biopsy punch, weighed, and incubated in PBS at 25° C. Excess solution was gently removed and the swelling ratio was calculated using the following equation: swelling ratio=(wet weight of hydrogel−dry weight of hydrogel)/dry weight of hydrogel.

Extraction of FAKI from hydrogels: Dry hydrogel weighing 2.5 mg was mixed with 0.5 ml of water followed by homogenization using Bullet Blender Bead Mill Homogenizer (Next Advance, Averill Park, NY). Homogenate was diluted with 0.5 mL of methanol to extract FAKI, and then centrifuged for 5 min at 5000 g. Sample recovery of >90% was attained and analyzed by HPLC and mass spectrometry (LC-MS) method as described below.

In vitro drug release profiles for FAKI from pullulan-collagen hydrogels. In vitro release kinetics of FAKI was studied to compare the two different template preparation methods. Dry hydrogels weighing 2.5 mg and containing 50 μg of FAKI were placed into a 25,000 MWCO dialysis membrane tube with 1 ml of PBS. Dialysis tube was sealed on both sides and then immersed in 9 ml of PBS in a vial. The vial was incubated at 37° C. with gentle agitation. Small aliquots were drawn periodically to quantify and determine the integrity of the FAKI released from hydrogels.

LC-MS analysis: Experiments were performed on an AB SCIEX 4000 QTRAP® LC-MS/MS System. The HPLC apparatus was from Shimadzu Prominence LC system, equipped with system controller CBM-20A, Binary LC-20AD pump, and SIL-20AC autosampler. HPLC was performed using the following specifications: mobile phase: 90% methanol/10% water/0.1% formic acid, column: Dionex, Acclaim 120 C8, 5 μm, 50×2.1 mm, flow rate: 0.3 ml/min, and the injection volume: 10 μL. The HPLC was directly coupled to an AB SCIEX 4000 QTRAP® triple quadrupole mass spectrometer with electrospray ionization. The mass spectrometer was operated in positive multiple reaction monitoring (MRM) mode, ion source: turbo spray, resolution: Q1 unit; Q3 unit, mass MRM transitions (m/z): 508.30>121.00.

Data analysis: The structural integrity of FAKI was determined by molecular weight and HPLC retention time. Cumulative release from in vitro experiments performed in triplicate was expressed as the mean±SD. 3.

Animals and splinted excisional and contact burn injury models.

Animals (mice): All animal procedures were approved by the Administrative Panel on Laboratory Animal Care at Stanford University and the US Army Medical Research and Material Command Animal Care and Use Review Office. Wild type female C57BL/6J mice 8-10 weeks old (The Jackson Laboratory, Bar Harbor, ME) were used to create either splinted full-thickness excisional or third degree burn wounds according to published methods (Wang et al., 2013; Wong et al., 2011b; Sultan et al., 2012).

Excisional wounding: For surgically-created excisional wounds, two full-thickness wounds (one wound on each side of the dorsal midline) were made with a 6-mm punch biopsy tool. Silicone rings that circumscribe the wound were sutured to the skin to prevent wound contracture (primary means of rodent wound healing) but to allow the wound to close by re-epithelialization (similar to human wound healing).

Burn wounding: Contact burn wounds were created only on one side in the dorsum with an aluminum rod heated to 100° C. in a hot water bath for 20 sec. Wounds were immediately cooled down with cold water for 30 sec. To simulate the routine clinical setting of full-thickness human burn injuries, we excised the necrotic tissues along the wound margins to the level of underlying subcutaneous fat 72 hrs after the initial injury. In both models, wounded animals were randomly separated into three groups and received either standard dressing (Tegaderm) or blank hydrogel or FAKI-laden hydrogel. Dressings and hydrogels were replaced every 2-3 days. Burn wounds were allowed to heal without splinting and hydrogels and bandages were changed every day for the first 3 days and then every other day thereafter. For some excisional wounds, FAKI dissolved in 10% DMSO were dripped directly on to the wound site daily for 10 days before cell lysates were collected for western blotting. All digital photographs were analyzed using NIH ImageJ software by two blinded investigators.

Hypertrophic scar model and local subcutaneous injection of FAKI: Incisional wounding and development of hypertrophic scars on the dorsum of mice were performed by previously described methods (Aarabi et al., 2007; Wong et al., 2011a). Animals were randomly assigned to receive 15, 75, or 150 μM concentrations of FAKI dissolved in 10% DMSO via daily local subcutaneous injection adjacent to the wound site. Animals that received 150 μM FAKI did not survive more than 2 days due to undetermined systemic complications. Specimens were harvested at Day 14 post-injury for histology and scar areas were quantified (FIG. 6).

Animals (mice): Red Duroc pigs were used to create thick, long-lived human-like scars upon deep dermal wounding according to published methods (Zhu K Q et al., Burns. 2003 November; 29(7):649-64. Burns; Zhu K Q et al., Wound Repair Regen. 2007 September-October; 15 Suppl 1:S32-9. Porcine skin has been shown to most similar to human skin (e.g., similar epidermal thickness, similar dermal-epidermal thickness ratio, hair follicle and blood vessel patterns. Seven female red Duroc pigs 6-8 weeks old, weighing 16-20 kg were used. Multiple 5×5 cm, 0.07 inch excisional wounds (FIG. 7B, and FIG. 7E inset) were created with an electric dermatome. Wounds were near full-thickness in the center and deep partial-thickness towards the periphery. Wounds were randomly assigned to control (no treatment), hydrogel only (placebo), or hydrogel with FAKI treatment.

Histological and immunofluorescent staining. Specimens were harvested at Day 17-post injury and Day 24 post-debridement for excisional and burn wounds, respectively, and fixed in 4% paraformaldehyde, dehydrated, and then paraffin-embedded. Hematoxylin & Eosin (H&E) and Masson's Trichrome staining was performed according to routine protocols. The percentage of blue area in the images of Masson's Trichrome staining was quantified using ImageJ. Immunofluorescent staining was performed using a primary antibody against mouse alpha-smooth muscle actin (α-SMA). Secondary antibodies conjugated to FITC were used and images were observed under a fluorescent microscope. The percentage of green area was quantified using ImageJ.

Western blotting. Western blotting was performed to study FAK expression and phosphorylation at tyrosine-397 in excisional wound lysates. Protein was collected and quantified using BCA assay. Equal amounts of protein were loaded in each well on precast 4% gels and subjected to SDS-PAGE. After transfer of proteins, nitrocellulose membranes were incubated with primary antibodies to either FAK (Cell Signaling, Danvers, Mass.) or p-FAK (Abcam, Cambridge, MA), followed by HRP-conjugated secondary antibody incubation. Chemiluminescent detection of antibodies was conducted according to the manufacturers' protocol. Band intensity was quantified using ImageJ.

CT-FIRE. Sections were stained for collagen and analyzed using CT-FIRE software. CT-FIRE software allows users to automatically extract collagen fibers from an image and quantify fibers with descriptive statistics including: fiber angle, length, straightness, and width. The program reads image files supported by MATLAB and extracts the individual collagen fibers via a combined method called CT-FIRE (named ctFIRE in the software implementation). The approach of CT-FIRE is described in Bredfeldt J S, Liu Y, Pehlke C A, et al (2014) Computational segmentation of collagen fibers from second-harmonic generation images of breast cancer. J Biomed Opt 19:16007-16007 which combines the advantages of the discrete curvelet transform (Candes E, Demanet L, Donoho D, Ying L (2006) Fast discrete curvelet transforms. Multiscale Model Simul 5:861-899) for denoising the image and enhancing the fiber edge features with the advantages of the fiber extraction (FIRE) algorithm[3] for extracting individual fibers.

Skin mechanical test. Three weeks after creating splinted excisional wounds, wound tissues were collected and mounted on an MTS Bionix® tensile tester for mechanical testing (MTS Systems, Eden Prairie, MN). Sample gauge distance was set at 10 mm, and sample thickness and width were measured manually. Skin tissues were stretched at a constant speed of 100 □m/second until breaking, and then true stress vs. true strain curves were plotted. Ultimate tensile strength (UTS) was determined as the maximal stress achieved before breaking and the strain corresponding to UTS was defined as critical strain. Young's modulus was calculated via linear least squares regression ($R2 \geq 0.99$).

Data analysis. Results are reported as mean±SD. Statistical differences were determined using one-way ANOVA with Tukey's posthoc test for multiple comparisons. Differences were considered statistically significant at $p<0.05$.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for promoting tissue healing, comprising:
   placing on a surface of the tissue a composition comprising a porous scaffold and a focal adhesion kinase (FAK) inhibitor fabricated for controlled release disposed in pores of the scaffold; and
   delivering to the surface of the tissue a dose of the FAK inhibitor effective to promote tissue healing, scar reduction, and hair growth at a controlled rate during a treatment time,
   wherein the FAK inhibitor is VS-6062 (PF-562271), a benzenesulfonate salt of PF-562271, PF-573228, TAE226 (NVP-TAE226), PF-03814735, PF-562271 HCl, GSK2256098, PF-431396, PND-431396, PND-1186 (VS-4718), Defactinib (VS-6063, PF-04554878), or Solanesol (nonaisoprenol).

2. The method of claim 1 wherein the porous scaffold comprises a hydrogel film.

3. The method of claim 2 wherein the hydrogel comprises a pullulan-collagen hydrogel.

4. The method of claim 1 further comprising reducing scarring of tissue.

5. The method of claim 1 further comprising promoting hair growth in the tissue.

6. The method of claim 1 wherein the composition is configured as a wound dressing.

7. The method of claim 1 wherein FAK inhibitor is disposed on a delivery surface of the composition.

8. The method of claim 1 wherein the controlled rate comprises a rapid release rate and a sustained release rate.

9. The method of claim 1 wherein the delivering step comprises delivering to the surface of the tissue the dose of the FAK inhibitor within about 24 hours after the placing step.

10. The method of claim 1 wherein the dose of the FAK inhibitor is delivered to the tissue surface over a period of up to about 96 hours.

11. The method of claim 1 further comprising removing the composition from the tissue surface.

12. The method of claim 1 further comprising repeating the placing and delivering steps at least 3 times.

13. The method of claim 1 further comprising repeating the placing and delivering steps at least 10 times.

14. The method of claim 1 further comprising delivering to the tissue from about 30% of the FAKI inhibitor in the composition to about 75% of the FAK inhibitor in the composition.

* * * * *